United States Patent
Hu

(10) Patent No.: US 10,713,788 B2
(45) Date of Patent: *Jul. 14, 2020

(54) SYSTEMS AND METHODS FOR EVALUATING ACCURACY IN A PATIENT MODEL

(71) Applicant: Smith & Nephew, Inc., Memphis, TN (US)

(72) Inventor: Yangqiu Hu, San Antonio, TX (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/511,458

(22) Filed: Jul. 15, 2019

(65) Prior Publication Data

US 2020/0005456 A1 Jan. 2, 2020

Related U.S. Application Data

(63) Continuation of application No. 16/163,316, filed on Oct. 17, 2018, now Pat. No. 10,354,381, which is a
(Continued)

(51) Int. Cl.
*G06T 7/00* (2017.01)
*G06T 17/00* (2006.01)
(Continued)

(52) U.S. Cl.
CPC .......... *G06T 7/0012* (2013.01); *G06T 7/0014* (2013.01); *G06T 7/10* (2017.01); *G06T 7/11* (2017.01); *G06T 7/12* (2017.01); *G06T 7/13* (2017.01); *G06T 7/33* (2017.01); *G06T 17/00* (2013.01); *G06T 17/20* (2013.01);
(Continued)

(58) Field of Classification Search
None
See application file for complete search history.

(56) References Cited

U.S. PATENT DOCUMENTS

| 5,408,409 A | 4/1995 | Glassman et al. |
| 6,205,411 B1 | 3/2001 | DiGioia, III et al. |

(Continued)

FOREIGN PATENT DOCUMENTS

| WO | 2011044442 A1 | 4/2011 |
| WO | 2012021862 A2 | 2/2012 |

OTHER PUBLICATIONS

Cootes et al. "Active-Shape Models—Their Training and Application" Jan. 1, 1995; Computer Vision and Image Understanding 61(1):38-59.
(Continued)

*Primary Examiner* — Idowu O Osifade
(74) *Attorney, Agent, or Firm* — Pepper Hamilton LLP

(57) ABSTRACT

Systems, devices, and methods are described for providing patient anatomy models with indications of model accuracy included with the model. Accuracy is determined, for example, by analyzing gradients at tissue boundaries or by analyzing tissue surface curvature in a three-dimensional anatomy model. The determined accuracy is graphically provided to an operator along with the patient model. The overlaid accuracy indications facilitate the operator's understanding of the model, for example by showing areas of the model that may deviate from the modeled patient's actual anatomy.

17 Claims, 17 Drawing Sheets

Related U.S. Application Data continuation of application No. 15/124,979, filed as application No. PCT/US2015/019580 on Mar. 10, 2015, now Pat. No. 10,140,703.

(60) Provisional application No. 61/950,610, filed on Mar. 10, 2014.

(51) Int. Cl.

| | |
|---|---|
| *G06T 19/00* | (2011.01) |
| *G06T 7/12* | (2017.01) |
| *G06T 17/20* | (2006.01) |
| *G06T 7/33* | (2017.01) |
| *G06T 7/10* | (2017.01) |
| *G06T 7/11* | (2017.01) |
| *G06T 7/13* | (2017.01) |
| *A61F 2/46* | (2006.01) |

(52) U.S. Cl.
CPC ...... *G06T 19/00* (2013.01); *A61F 2002/4633* (2013.01); *G06T 2207/10004* (2013.01); *G06T 2207/30008* (2013.01); *G06T 2210/41* (2013.01)

(56) References Cited

U.S. PATENT DOCUMENTS

| | | |
|---|---|---|
| 10,140,703 B2 | 11/2018 | Hu |
| 2009/0076371 A1 | 3/2009 | Lang et al. |
| 2011/0282473 A1 | 11/2011 | Pavlovskaia et al. |
| 2012/0063668 A1 | 3/2012 | Zalmanson |
| 2013/0166256 A1 | 6/2013 | Wirx-Speetjens et al. |
| 2014/0328524 A1 | 11/2014 | Hu et al. |

OTHER PUBLICATIONS

European Search Report for EP 15761777.0 dated Aug. 31, 2017.

Fripp et al. "Automatic Segmentation and Quantitative Analysis of the Articular Cartilages From Magnetic Resonance Images of the Knee" Jan. 1, 2010; IEEE Transactions on Medical Imaging 29(1):55-64.

Fripp et al. "Automatic segmentation of the bone and extraction of the bone-cartilage interface from magnetic resonance images of the knee" Mar. 21, 2007; Physics in Medicine and Biology 52(6):1617-1631.

Fripp et al. "Automatic Segmentation of the Bones from MR Images of the Knee" Apr. 1, 2007; IEEE 4th Proceedings pp. 336-339.

International Search Report and Written Opinion for PCT/US2015/019580; dated Jun. 1, 2015.

Kelemen et al. "Three-dimensional Model-based Segmentation of Brain MRI" Jun. 26-27, 1998; IEEE Proceedings pp. 4-13.

SYSTEMS AND METHODS FOR EVALUATING ACCURACY IN A PATIENT MODEL

CROSS-REFERENCE TO RELATED APPLICATIONS

This application is filed as a continuation application claiming the benefit of priority from U.S. patent application Ser. No. 16/163,316, filed Oct. 17, 2018 and entitled "Systems and Methods for Evaluating Accuracy in a Patient Model," which is a continuation application claiming the benefit of priority from U.S. patent application Ser. No. 15/124,979, filed Sep. 9, 2016, which is a U.S. national stage filing under 35 U.S.C. § 371 of International Application No. PCT/US2015/019580, filed Mar. 10, 2015, which in turn claims the benefit of U.S. Provisional Application No. 61/950,610 filed Mar. 10, 2014, the contents of each of which is hereby incorporated by reference herein in its entirety.

BACKGROUND

Patient specific modeling is used in connection with surgical and orthopedic procedures to plan a surgery or to design instruments and implants for the surgery. A patient specific model allows a surgeon to account for variation in anatomy between patients by first modeling the portion of the body at which the surgery is carried out. The surgical procedure can be precisely planned by tailoring the approach and instruments to particular variations in the patient's anatomy that may otherwise cause difficulties during a standard procedure. As a first step in the process, the patient's anatomy is imaged by standard medical technology, for example using an MRI or a CT scanning machine, in order to obtain a data set that is representative of the patient's anatomy. The data set that is obtained indicates any particular variations or nuances in the patient's anatomy, and processing that data can provide a surgeon with a detailed map of the relevant body portion ahead of time.

The imaging data obtained from the patient's anatomy is processed to create a model of the patient's anatomy that is used to plan the procedure. The raw data set can be processed in a number of different ways, including filtering, interpolation, sampling, and other data processing procedures that turn the data into a digital anatomy model for the surgeon's use. One particular processing approach is image segmentation, in which the full data set is analyzed in blocks, with each block representing a different area of the relevant anatomy. These processing techniques, including segmentation, can introduce errors into the model as a result of the estimation that compresses and otherwise processes the data. For example, there may be rounding or smoothing effects that create a smooth surface in the model that does not account for the deviations from that smooth surface that are actually present in the patient's anatomy. For some procedures, these processing errors are of particular interest when they occur at boundary regions between different types of tissue in the model. At these boundary regions, the data processing algorithm may not produce a model in which the division between two tissues is precisely estimated. Additionally, processing errors may be of interest when they occur at an anatomical landmark such as the medial condyle, lateral condyle, or Whiteside's line. At anatomical landmarks, the data processing algorithm may incorrectly identify a landmark location due to errors in the model.

The amount of processing performed on a raw data set of imaging data is correlated with the number of potential estimation errors introduced to a patient model. The more times or ways in which the data is sampled, smoothed, or estimated, the greater the chance will be that there are errors and deviations introduced into the model that do not completely reflect the patient's anatomy with precision. When these estimations and deviations occur in areas of the anatomy that are important for the surgical procedure being planned, they may lead to complications during the surgery. For example, a surgical guide or implant that does not correctly match the patient's bone may result in longer surgeries due to poorly fitted instrumentation or an abandonment of the surgery altogether.

For some procedures, patient implants and instrumentation such as surgical guides are designed to match a specific patient's bone anatomy. In these cases, accurate models can be helpful to create an implant or surgical guide that will closely interface with the patient's bone. Any deviations or variations between the model and the actual anatomy, particularly in areas where the implant or surgical guide interfaces with the bone, may reduce the effectiveness of the surgical procedure. For such applications, it would be helpful to have an indication not only of the patient's estimated anatomy, but also an indication of how closely the modeled anatomy maps to the real anatomy. Providing a surgeon or other operator with indications of accuracy directly on an anatomy model would be beneficial and could lead to early error detection and improvement of surgical procedures.

SUMMARY

Disclosed herein are systems, devices and methods for patient modeling and, in particular, for analyzing bone models to provide an indication of the accuracy of the model. For example, the systems, devices and methods discussed herein may analyze gradients at tissue interfaces in the model to determine accuracy of bone surface estimation. The systems, devices, and methods discussed herein may also determine the curvature of areas of the modeled bone surface to identify potential inaccuracies in the location of convex, concave, and transition areas of the bone surface. The approaches discussed herein provide bone models with indications of the accuracy of the models overlaid directly on the modeled anatomy. Additionally, the approaches discussed herein allow for improved identification of anatomical landmarks such as the medial condyle, lateral condyle, and Whiteside's line. The systems, devices and methods provide an operator with an efficient approach in identifying potentially weak areas of the model. In particular, the operator is able to see right on the model which areas of the modeled bone may deviate from the patient's anatomy. Presurgical planning and device design can then be done while taking this information into account.

In one aspect, a method for indicating accuracy of image segmentation in a patient model includes creating a three-dimensional bone surface model of a portion of a patient's bone from imaging data, calculating a first signal intensity gradient between a first point on a surface of the three-dimensional model and a second point spaced from the surface along a line extending from the surface at the first point, and marking the first point on the three-dimensional model if the first gradient exceeds a first threshold. In certain implementations, the line is normal to the surface at the first point.

In certain implementations, the second point is spaced from the surface at a location outside the modeled bone. The second point may also be spaced from the surface at a location within the modeled bone. The method may also include calculating a second signal intensity gradient between the first point and a third point spaced from the surface along the line. For such a method, the second point is spaced from the surface at a location outside the modeled bone, the third point is spaced from the surface at a location within the modeled bone, the first gradient indicates a signal intensity change outward from the surface, and the second gradient indicates a signal intensity change inward from the surface.

In certain implementations, the method includes determining whether each of the first and second gradients exceeds a threshold. The threshold for both the first and second gradients may be the first threshold, or the method may include determining whether the first gradient exceeds the first threshold and determining whether the second gradient exceeds a second threshold. After determining whether each gradient exceeds a threshold, the method may include the first point if both of the first and second gradients exceed a threshold. The method may also include marking the first point if either one of the first and second gradients exceeds a threshold. The method may include displaying the first point in a first color if both of the first and second gradients exceed a threshold, displaying the first point in a second color if only one of the first and second gradients exceeds a threshold, and displaying the first point in a third color if neither of the first and second gradients exceeds a threshold. The second color may indicate whether the first or second gradient is the one gradient that exceeds a threshold.

In certain implementations, marking the first point includes displaying a graphical indicator at the first point on the three-dimensional model.

In certain implementations, the method includes calculating a plurality of signal intensity gradients, each signal intensity gradient corresponding to a point on the surface of the three dimensional model. The method determines whether each of the plurality of signal intensity gradients exceeds a threshold. The method also determines whether a minimum number of signal intensity gradients exceeding a threshold is met. If the minimum number is not met, the imaging data is reprocessed to create a new three-dimensional model and/or an alert is displayed to an operator. Signal intensity gradients corresponding to points of interest in the three-dimensional model may be weighted before determining if the minimum number is met. For example, in some implementations the points of interest correspond to contact points between patient-matched implants or surgical guides and the modeled bone and/or correspond to points located in areas on the modeled bone that exhibit variation among patients.

In certain implementations, a first vector line is displayed extending from the surface of the three-dimensional model at the first point. The first vector line may be displayed in response to a first user selection of the first point. When the first vector line is displayed, a second user selection of an alternate point on the surface of the three-dimensional model may be received, in which case the method includes displaying a second vector line extending from the surface of the three-dimensional model at the alternate point in response to the second user selection.

In one aspect, a method for indicating accuracy of image segmentation in a patient model includes creating a three-dimensional bone surface model of a portion of a patient's bone from imaging data, determining curvature of the modeled bone surface at a plurality of points in the three-dimensional model, and marking each of the plurality of points in the three-dimensional with an indication whether each point is located within a concave or convex portion of the surface.

In certain implementations, marking each of the plurality of points includes displaying points located within a concave portion of the surface in a first color and displaying points located within a convex portion of the surface in a second color. The method may also include identifying transition points between concave and convex portions of the surface. Each of the transition points is then marked in the three-dimensional model. Marking each of the transition points may include displaying a graphical indicator at each of the transition points and/or marking each of the transition points in a color that is different than colors of concave and convex portions of the model.

In certain implementations, the method includes determining if a minimum number of transition points is met. The imaging data may be reprocessed to create a new three-dimensional model if the minimum number is met, and the method may display an alert to an operator if the minimum number is met. Points of interest in the three-dimensional model may be weighted before determining if the minimum number is met. For example, the points of interest may be located in areas of the model that are not expected to contain transition points.

In one aspect, a system for indicating accuracy of image segmentation in a patient model includes means for creating a three-dimensional bone surface model of a portion of a patient's bone from imaging data, means for calculating a first signal intensity gradient between a first point on a surface of the three-dimensional model and a second point spaced from the surface along a line extending from the surface at the first point, and means for marking the first point on the three-dimensional model if the first gradient exceeds a first threshold. In certain implementations, the line is normal to the surface at the first point.

In certain implementations, the second point is spaced from the surface at a location outside the modeled bone. Alternatively, the second point may be spaced from the surface at a location within the modeled bone.

In certain implementations, the system includes means for calculating a second signal intensity gradient between the first point and a third point spaced from the surface along the line. In such implementations, the second point is spaced from the surface at a location outside the modeled bone, the third point is spaced from the surface at a location within the modeled bone, the first gradient indicates a signal intensity change outward from the surface, and the second gradient indicates a signal intensity change inward from the surface. The system may also include means for determining whether each of the first and second gradients exceeds a threshold. This system may include means for determining whether each of the first and second gradients exceeds the first threshold, or it may include means for determining whether the first gradient exceeds the first threshold and means for determining whether the second gradient exceeds a second threshold. In such a system, the means for marking the first point includes means for marking the first point if both of the first and second gradients exceed a threshold. Alternatively, the means for marking the first point includes means for marking the first point if either one of the first and second gradients exceeds a threshold. The means for marking the first point may also include means for displaying the first point in a first color if both of the first and second gradients exceed a threshold, means for displaying the first point in a second color if only one of the first and second gradients exceeds a threshold, and means for displaying the first point in a third color if neither of the first and second gradients exceeds a threshold. The second color may indicate whether the first or second gradient is the one gradient that exceeds a threshold.

In certain implementations, the means for marking the first point includes means for displaying a graphical indicator at the first point on the three-dimensional model.

In certain implementations, the system includes means for calculating a plurality of signal intensity gradients, each signal intensity gradient corresponding to a point on the surface of the three dimensional model. The system includes means for determining whether each of the plurality of signal intensity gradients exceeds a threshold and means for determining whether a minimum number of signal intensity gradients exceeding a threshold is met. The system includes means for reprocessing the imaging data to create a new three-dimensional model if the minimum number is not met and/or means for displaying an alert to an operator if the minimum number is not met. The system may also include means for weighting signal intensity gradients corresponding to points of interest in the three-dimensional model before determining if the minimum number is met. The points of interest may correspond to contact points between patient-matched implants or patient-matched cutting blocks and the modeled bone and/or correspond to points located in areas on the modeled bone that exhibit variation among patients.

In some implementations, the system includes means for displaying a first vector line extending from the surface of the three-dimensional model at the first point. Such systems include means for receiving a first user selection of the first point, means for displaying the first vector line in response to the first user selection, means for receiving a second user selection of an alternate point on the surface of the three-dimensional model after the first vector line is displayed, and means for displaying a second vector line extending from the surface of the three-dimensional model at the alternate point in response to the second user selection.

In one aspect, a system for indicating accuracy of image segmentation in a patient model includes means for creating a three-dimensional bone surface model of a portion of a patient's bone from imaging data, means for determining curvature of the modeled bone surface at a plurality of points in the three-dimensional model, and means for marking each of the plurality of points in the three-dimensional with an indication whether each point is located within a concave or convex portion of the surface.

In certain implementations, the means for marking each of the plurality of points includes means for displaying points located within a concave portion of the surface in a first color and means for displaying points located within a convex portion of the surface in a second color. The system may also include means for identifying transition points between concave and convex portions of the surface, and it may include means for marking each of the transition points in the three-dimensional model. The means for marking each of the transition points includes means for displaying a graphical indicator at each of the transition points and/or means for displaying each of the transition points in a color that is different than colors of concave and convex portions of the model.

In certain implementations, the system includes means for determining if a minimum number of transition points is met. The system may include means for reprocessing the imaging data to create a new three-dimensional model if the minimum number is met and/or means for displaying an alert to an operator if the minimum number is met. The system may also include means for weighting points of interest in the three-dimensional model before determining if the minimum number is met. The points of interest may be located in areas of the model that are not expected to contain transition points.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout.

DETAILED DESCRIPTION

The systems, devices, and methods described below involve analyzing patient anatomy models to determine model accuracy. Patient bone models are discussed below, in particular knee joint models, but the approaches disclosed are applicable to other bone models and models for other types of tissue. The model accuracy determinations are described with regards to analyzing gradients and surface curvature. Other accuracy parameters may be used instead of or in addition to these metrics.

The approaches disclosed herein provide an operator with a model of a patient's bone anatomy and an assessment of the accuracy of that bone model. In particular, any errors that may be introduced into that model as a result of segmentation and data processing are flagged for the operator. For example, when manually segmenting an MRI image, the operator may place a segmentation line away from the actual bone/cartilage boundary, which may cause error in the resulting bone model. The incorrectly placed segmentation line may cause error of approximately 0.25 mm to 0.50 mm, which can then translate into error in the bone model. The systems and methods described herein may flag this deviation so that the operator recognizes there is segmentation error in the bone model. The model is displayed for the operator with indications of the determined accuracy layered directly onto the model. This layered display provides the operator with indications of which areas of the model may or may not reliably reflect the actual patient anatomy. By providing this indication, the model facilitates the operator's presurgical planning and raises flags for the operator when further data processing or other modeling estimation is needed in order to obtain a more accurate model. The model may also allow an operator to identify chronic areas where MRI or other image data is not being accurately segmented. The bone model may be used to produce an implant or surgical guide for a surgical procedure. For example, the bone model may be used to design surgical cutting guides for a proximal end of a tibia and a distal end of a femur to be used during a total knee replacement surgery.

Figure 1:
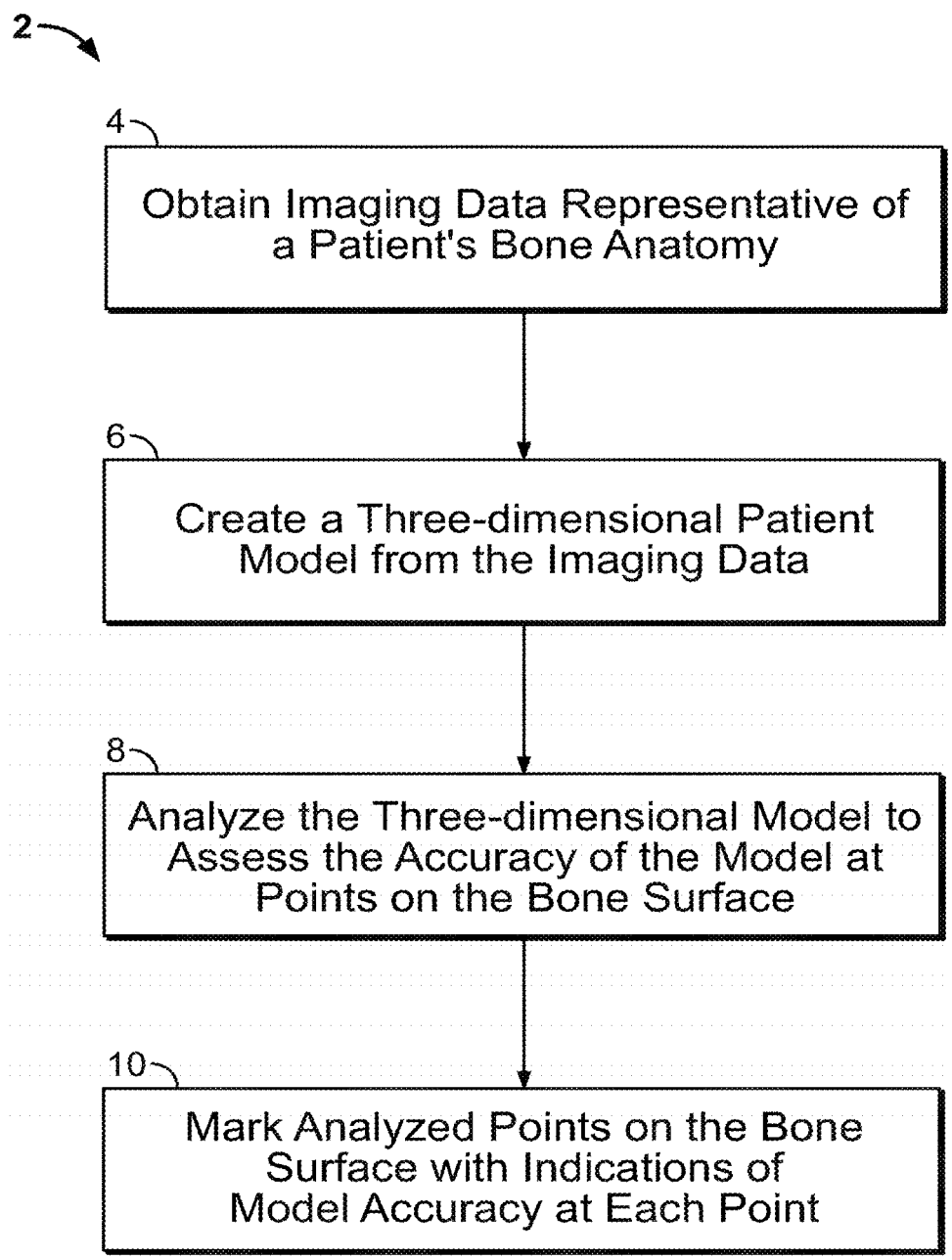
FIG. 1 shows an illustrative process for assessing the accuracy of a bone model.

FIG. 1 shows a process 2 for creating a model of a patient's bone anatomy and assessing the accuracy of the modeled bone. The method 2 begins when imaging data representative of the patient's bone anatomy is obtained at step 4. The imaging data may be obtained by any suitable medical imaging technique, for example by MRI, CT scan, or another suitable imaging approach. For purpose of illustration, the embodiments disclosed herein are described with respect to a patient's knee joint anatomy, but other areas of anatomy, including other bones, organs or any other portion of the patient's body may serve as a suitable model. The imaging data that is obtained from the patient's anatomy is processed at step 6 to create a three-dimensional model from the imaging data.

The processing at step 6 is carried out by modeling software programmed on a computer component, for example a processor or microprocessor. The processor receives the obtained image data and transforms or otherwise processes the imaging data to produce a three-dimensional representation of the patient anatomy. Creating the three-dimensional patient model may include any number of processing operations, for example decimating, oversampling, filtering, transforming or otherwise manipulating the imaging data. In certain implementations, the creation of the three-dimensional patient model includes image segmentation that breaks up the imaging data into disjoint blocks and processes each block individually to create a representation of that block in the three-dimensional model. In some embodiments, the segmentation is performed manually by the operator. In this case, the operator may visually identify boundaries between bone and other tissues such as cartilage. The operator then draws a boundary that indicates to the processor that the image is to be segmented based on the boundary. The various processing algorithms may include estimation that reduces the amount of data and potentially compresses the data set to allow the patient model to be more easily transmitted than the full set of obtained imaging data.

To process the image data, the modelling software creates a volume model from the raw or preprocessed image data. For example, the modelling software may use MRI data slices in a sagittal plane that are spaced apart from one another by a set distance to create the volume model. Alternatively, or additionally, the modelling software may use MRI data slices in a coronal plane or an oblique plane that are spaced apart from one another by a set distance to create the volume model. The MRI data is then used to create interpolated parallel MRI data slices for the volume model. Specifically, the interpolated parallel MRI data slices represent an approximated MRI data slice between two slices for which MRI data is available. The interpolated parallel MRI data slices may be created by evaluating an average signal intensity value between two consecutive MRI data slices, although any suitable interpolation method may be used. In addition, any number of interpolated MRI data slices may be created between two MRI data slices for which MRI data is available. Creating more interpolated parallel MRI data slices may increase the resolution of the volume model. The interpolated parallel MRI data slices may additionally be smoothed after interpolated signal intensity values are evaluated.

After the interpolated parallel slices are created, the volume model may be manipulated to create intersections or cuts for displaying cross-sections of the volume model. In particular, a cross section at an oblique angle or perpendicular to the MRI data slices may be generated. The cross-section of the volume model may include data from multiple MRI data slices in addition to data from interpolated MRI data slices. U.S. Patent Application Publication No. 2014-0328524 describes systems and methods for creating oblique cross sections from MRI data slices and interpolated parallel slices and is hereby incorporated by reference herein in its entirety.

As a result of the processing that occurs at step 6, the three-dimensional patient model that is created may vary slightly from the patient's actual bone anatomy in various areas of the model. Particularly in the case of image segmentation in which a region of the anatomy is estimated across a given block of the patient model, portions of that region may not completely align with the underlying anatomy. The systems and methods disclosed herein identify the areas where those variances occur and notifies the operator of the variance so that the operator may take into account when planning an orthopedic surgery or designing a patient-matched device (e.g., using manual image segmentation). At step 8, the created three-dimensional model is assessed for accuracy to identify any such regions of potential variation or error in the model. This analysis compares the three-dimensional model to the original imaging data that was used to create the model and identifies any areas of discrepancy that may exist between the two. The analysis that determines the accuracy of the model may include any suitable comparisons between the model and the imaging data. Two examples of such processing are calculation of signal intensity gradients at the surface of the model to identify areas where the estimated surface of the model either aligns or does not align with the tissue interfaces represented by the underlying imaging data. A second approach is identifying curvature of the surfaces of the three-dimensional model. The curvature is analyzed to identify inflection or transition points between concave and convex sections of the bone, particularly to identify those points that occur in areas where those transitions normally are not found in the anatomy. The curvature may also be analyzed to identify portions of the bone where convex or concave surfaces appear in the model where they would not normally be expected in the underlying patient's bone.

Once the model is analyzed in step 8, and areas of potential inaccuracy are identified in the model, the model is presented to the user with the analyzed points marked at step 10. The model that is displayed to the user at step 10 includes both the full model of the anatomical shape and contours that is created at step 6 from the imaging data, as well as overlaid indications of model accuracy at each point from the analysis in step 8. This provides the user with an indication, in parallel with the actual model, of the accuracy of the model as a whole, as well as relative accuracy of portions of the model relative to others. The points may be shaded or otherwise marked with graphical indicators to indicate the areas where accuracy if the model is determined to either be high or low.

The analyzed points marked in step 10 provide the user with a useful guide and insight into the readability of the modeling method 2. This indication of accuracy provides the user with a full picture of the modeled anatomy compared to a display of the model alone, or a display of the mode with a separate read out of accuracy statistics. Not only does the operator see the model itself, with the shapes and contours of the bone, but the operator also sees indications of points where that modeled shape and contour may vary from the anatomy. That indication is useful as the operator plans a surgery or designs an implant or surgical guide to fit the bone, particularly in the areas of the anatomy where the surgery is carried out or the implant or surgical guide is designed to fit closely.

In addition to marking the analyzed points in step 10 with indications of model accuracy, the systems and methods discussed herein may also perform quantitative analysis on the degree of overall model accuracy indicated by those points. For example, a minimum number of points may be required to be determined as accurate in order for the model to be accepted. If more than a set number of points are determined to be inaccurate by the analysis, for example by the analysis performed at step 8, then the model may be rejected to create a new patient model, for example at step 6, by reprocessing the original imaging data obtained at step 4. In other implementations, the model may not be automatically rejected but instead the user is provided with an indication that a minimum number of inaccurate points was exceeded. The user is then provided with an option to change the model or otherwise adjust the parameters of the model in order to improve the accuracy to an acceptable level.

Figure 2:
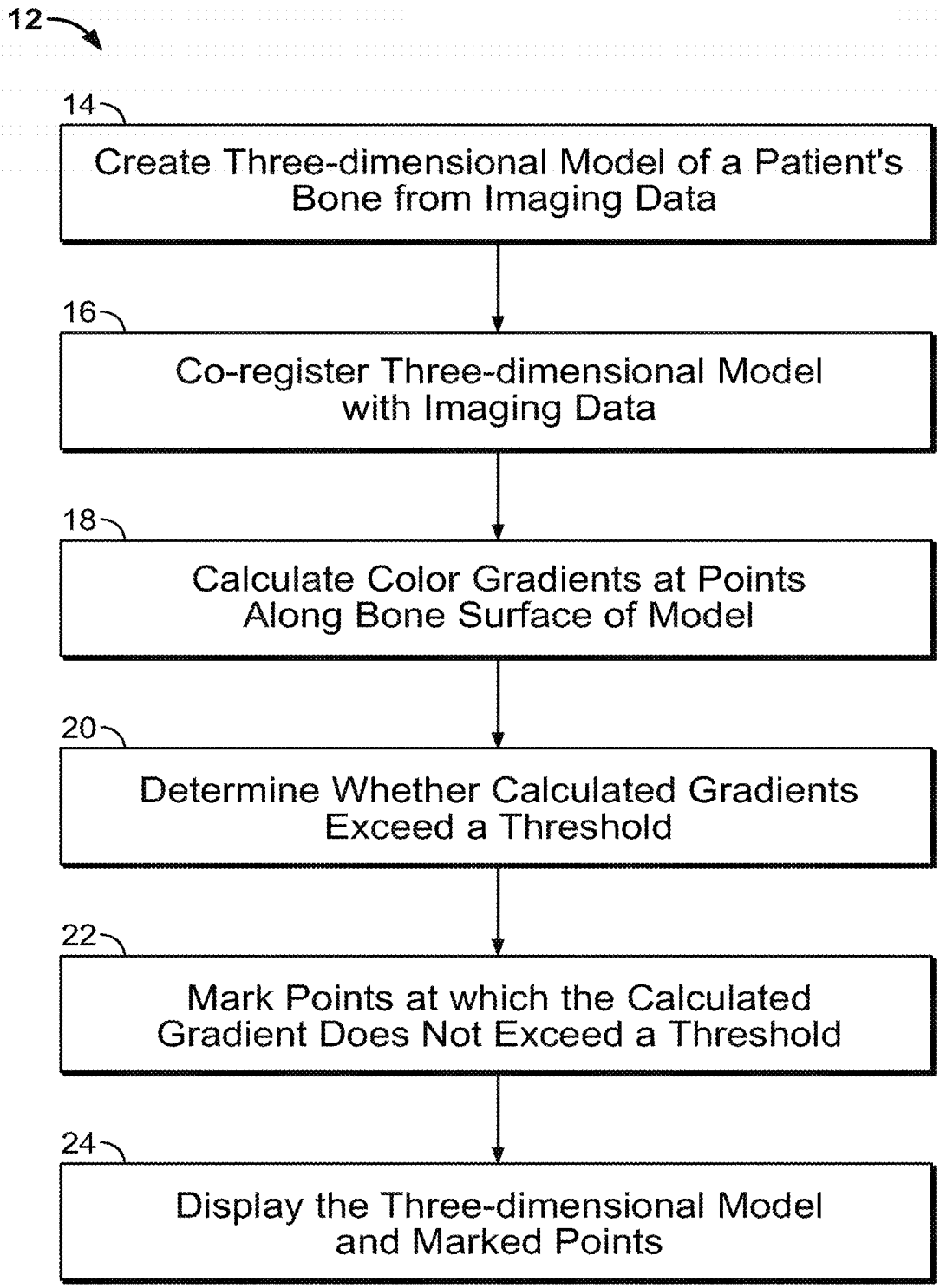
FIG. 2 shows an illustrative process for assessing the accuracy of a bone surface model by calculating gradients at points along the surface of the model.

FIG. 1 shows a general approach to patient modeling that includes indicators of the model accuracy overlaid on the model provided to the user. The different processing approaches and model analysis used to determine that accuracy representation may vary, but in each case a two-level display is presented to the operator. The method by which the model itself is created may vary, and the analysis that is performed on the created model may vary. One example of the analysis for accuracy assessment is an analysis of gradients at the surface of the bone shown in the model. This approach is illustrated in the method 12 in FIG. 2.

Method 12 begins at step 14 in which a three-dimensional model of the patient's bone is created from imaging data. The process of step 14 may be substantially similar to that described above with respect to step 6 of FIG. 1. As part of creating the model in step 14, the processing logic identifies the surface of the bone represented by the imaging data. This modeled surface is often a useful component of the model, because it can be used to determine where to approach the bone in a surgery or to define contours of corresponding instrumentation and implants designed to interface intimately with the bone. The bone surface is estimated within the model by analyzing the imaging data to define separations between the data inside the bone and outside the bone. This may include cortical bone/cartilage interfaces as well as bone/synovial interfaces. These separations may be characterized by a difference in signal density, signal intensity, signal frequency, wavelength or any other difference in the signal that is received when the imaging data is obtained. When the imaging data is processed to create the three-dimensional model, the processing logic includes algorithms that approximate the precise location of the surface interface between the bone and surrounding tissue. Because the surfaces can be a useful part of the subsequent surgery carried out on the anatomy, the location of this estimated surface can be a focus of the model analysis that determines the accuracy of the model compared to the anatomy imaging data.

In order to assess the accuracy of the location of the patient's bone in a three-dimensional model, the models and particularly some surface interfaces are compared with the imaging data from which the model was created. In step 16, the three-dimensional model is co-registered with the imaging data. In some embodiments, step 16 is optional because the three-dimensional model and the imaging data may be co-registered when the three-dimensional model is created. For example, a three dimensional surface model may be created from a volume model which contains the MRI data slices and interpolated MRI data slices. Because both the surface model and the volume model have the same coordinate system, they may be automatically co-registered with each other at the time of creation of the surface model. For the co-registration, the imaging data and three-dimensional model are aligned with each other to compare areas of the model with the surrounding areas of the imaging data and determine the degree of agreement between the model and the data.

Once the three-dimensional model and the imaging data are co-registered, the corresponding areas of the two data sets are compared to determine their alignment. One method of comparison is evaluating differences in the color density between the surface of the bone in the model and surrounding areas. In a grayscale visualization, for example obtained from MRI data, the bone that is imaged, particularly cortical bone, will exhibit a dark color. Surrounding soft tissue, such as muscle, ligaments, cartilage and other tissues, will have a relatively light color compared to the dark contrast of the bone. By analyzing the points at which the color changes from dark to light, and comparing the model to those contrasts in the imaging data that underlies the model, the processing logic can determine whether or not the estimated surface of the bone or the cartilage surface in the model is accurate. One approach to assess the color change at the modeled surface is to calculate gradients at points at the bone surface in the model. The gradients indicate whether or not a given point on the surface of the model is correctly aligned with the surface of the bone represented in the imaging data, or whether it is positioned either within the bone or outside the bone. A high gradient between the modeled surface and the imaging data towards the inside of the bone indicates that the surface point is a lighter color than the cortical bone, which is desired. Likewise, a high gradient between the surface point and tissues outside the bone will indicate that there is also a difference in coloring between the surrounding soft tissues and the surface point. The presence of both of these gradients at a modeled surface point is an indication that the modeled surface is at an accurate transition point between the dark bone and the light surrounding tissue. If the gradient is too small from the surface point towards either the dark bone tissue or light surrounding tissues, it is an indication that the surface point is placed either too near to the cortical bone or too near to the surrounding soft tissue.

At step 18, gradients are calculated at points along the surface of the bone model using the imaging data from which the model was created. The imaging data includes grayscale information in the areas around the surface. In some images such as MRI images, cortical bone is darker and fluids are brighter. In other images such as CT images, cortical bone is brighter and fluids are darker. The gradients are calculated based on differences in the grayscale data from the points at the surface of the model to points in the near vicinity of the surface along a line that is at an angle from the surface in the model. For example, grayscale gradients may be calculated along a line that is normal to the surface of the model. However, one of skill in the art will recognize that the gradients may be calculated along a line that is at any suitable angle from the surface of the model. These gradients may be calculated as differences between the grayscale at the surface points and points lying just outside the bone, gradients between the surface grayscale and points lying just inside the bone, or both. In either case, the presence of an appreciable gradient indicates that the modeled surface is accurately estimated, as it is expected to be located at a transition point between different tissues that exhibit different grayscales in the imaging data. If there are not relatively large gradients found in the calculations from step 18, the surface estimation may be off from the actual anatomy as the two points used to calculate the gradient lie within the same tissue rather than different tissues.

In order to determine whether or not the gradients calculated at step 18 indicate accurate or inaccurate bone surface estimation, the gradients are compared to a threshold at step 20. The threshold is a set or user-adjustable level that is determined to be a grayscalc gradient that would indicate an acceptable difference between bone tissue and surrounding soft tissue in the bone model. If gradients are calculated for both points lying outside and within the bone model, two different gradients may be compared to the threshold for a single point on the surface, the first indicating the gradient moving from the surface to surrounding tissue, and the second indicating the gradient moving from the surface to the bone tissue. In some implementations, these two gradients are each compared to the same threshold to make the determination at step 20. In alternative implementations, each gradient may be compared to a separate threshold, one for outside gradients and one for inside gradients. When the threshold determinations are examined to determine whether or not the surface placement is accurate, the presence of two gradients indicates that the surface is accurately located at a transition point between the dark bone and the light surrounding tissue. If no gradient is found, the analysis determines that the surface is inaccurately placed within only one type of tissue, either light surrounding tissue or dark bone tissue. In some implementations, an intermediate determination is made if only one of the two gradients is determined to exceed a threshold, as that determination indicates that the surface is close but not quite as accurate as an alternate surface placement may be.

The points that are determined not to have gradients exceeding a threshold at step 20 indicate areas where surface placement is inaccurate and that the model at those points deviates from the patient's anatomy. These points are marked at step 22 to indicate to the user that the model shown for those areas may not be adequately accurate. By marking the points for which the calculated gradient does not exceed the threshold, the patient model provides not only a representation of patient anatomy, but also an indication of areas where that model may be weak. The display of the model and the marked points is provided to the user at step 24. Once the model is displayed, the user may analyze the model, in particular the location of the marked points where inaccuracies are located, and determine if the model is sufficient to plan a surgery or design an implant or surgical guide, appropriately based on the accuracy of the model. The operator may also determine that slices of the image data need to be re-segmented if the error in the model is determined to be above a predetermined threshold. The model and indicators presented to the user is described in more detail in the FIGS. 3-11.

Figure 3:
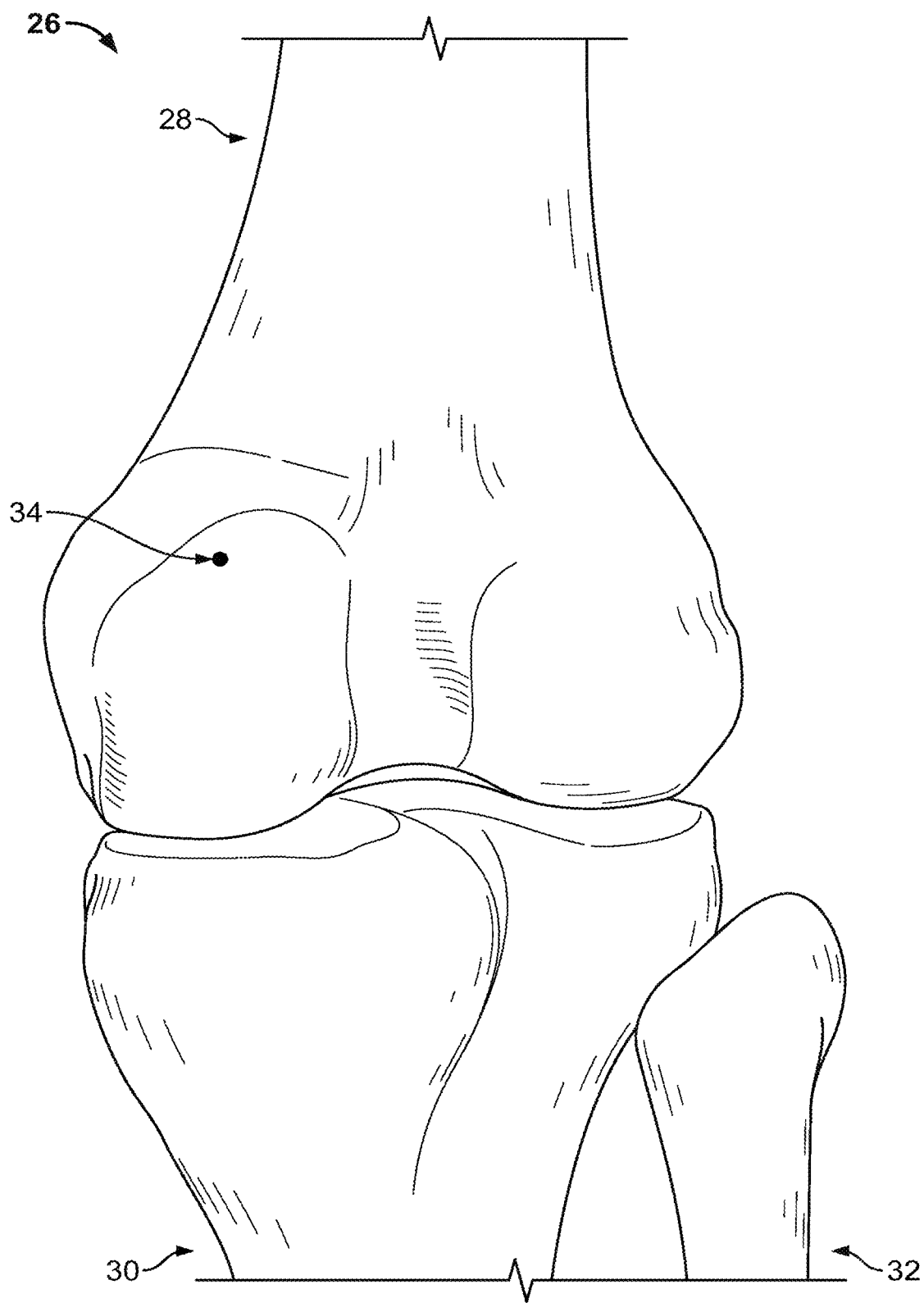
FIG. 3 shows an illustrative knee bone model with a surface point used for evaluating accuracy by calculating gradients.

FIG. 3 shows a bone model 26 of a patient's knee joint. The bone model 26 is created from imaging data collected of the patient's anatomy, for example a model that may be created at step 14 in the method 12 shown in FIG. 2. The model 26 includes a femur 28, a tibia 30 and a fibula 32. Such a model may be used in pre-operative planning to plan a surgery on the knee joint shown in the model 26 or to design an implant to replace one or more of the femur 28 and the tibia 30. The model may also be used for designing a patient-matched cutting guide to guide resection of the femur or tibia. In addition to displaying the estimation of a patient's anatomy in the model 26, the systems and methods disclosed herein add indications of the accuracy of each area of the bone depicted in the model 26 to improve the operator or surgeon's pre-operative planning. For example, points along the surfaces of the bones shown in the model 26 are analyzed, such as the point 34, in order to determine how closely each bone surface resembles the underlying patient anatomy.

Figure 4:
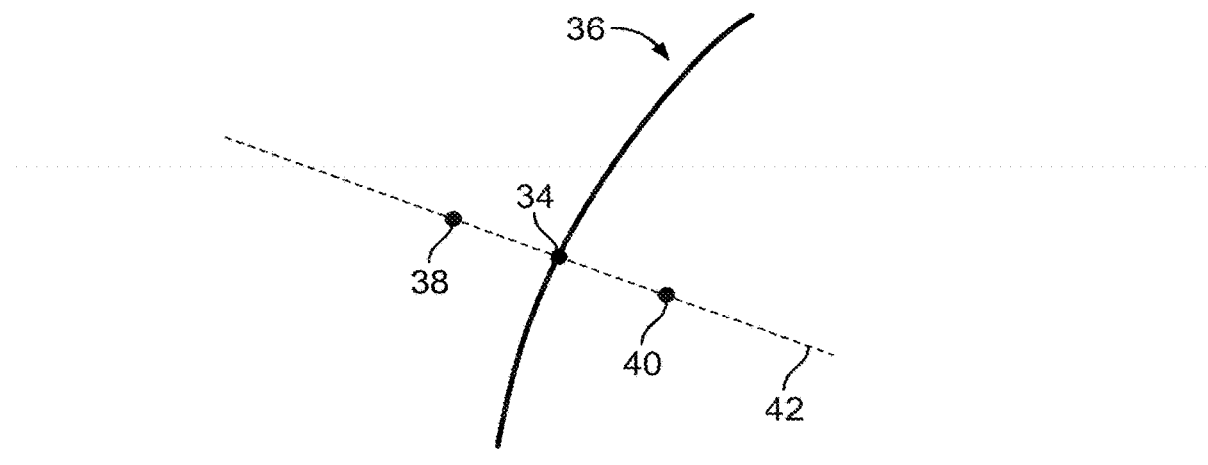
FIG. 4 shows a graphical representation of the point of the bone model in FIG. 3 used in calculating a gradient at the surface of the patient bone model.

An illustration of the location of point 34 in the model 26 and the points used to calculate gradients at the point 34 is shown in FIG. 4. Point 34 is located on the estimated surface 36 of the femur 28 in the model 26. The surface 36 is an estimation of the location of the patient's bone surface based on the imaging data processing used to create the model 26. In order to determine the accuracy of the placement of the surface 36, the point 34 is analyzed using the grayscale values of the imaging data in the vicinity of the point 34 to determine whether or not the estimated surface 36 is an accurate representation of the transition from bone to soft tissue in the patient's anatomy.

In order to calculate the gradients used to analyze the point 34, a line 42 is estimated normal to the surface 36 at the point 34. If the surface 36 is accurately located, the grayscale values of imaging data used to create the model 26 exhibit a change from point 34, moving in either direction along the line 42. In particular, the grayscales become darker moving into the bone from the surface 36, for example to point 40. The grayscales become lighter moving outside the bone into the estimated soft tissue from the surface 36, for example to the point 38.

In order to determine the accuracy of the placement of the surface 36 at point 34, the grayscales of point 34 and each of points 38 and 40 are subtracted to calculate a gradient moving both into and out of the bone. For example, for a gradient moving into the bone, the absolute value of the difference between the grayscale imaging data values at point 34 and 40 indicates whether or not the two points lie in different types of tissue. Likewise, the absolute value of the difference between the gray scale at point 34 and point 38 provides the same indication moving outside of the bone in the model 26. To provide an illustration of the interplay between the model 26 and the underlying imaging data grayscale values, the surface 36 is overlaid with a grid 44 of imaging data grayscale values in FIG. 5.

Figure 5:
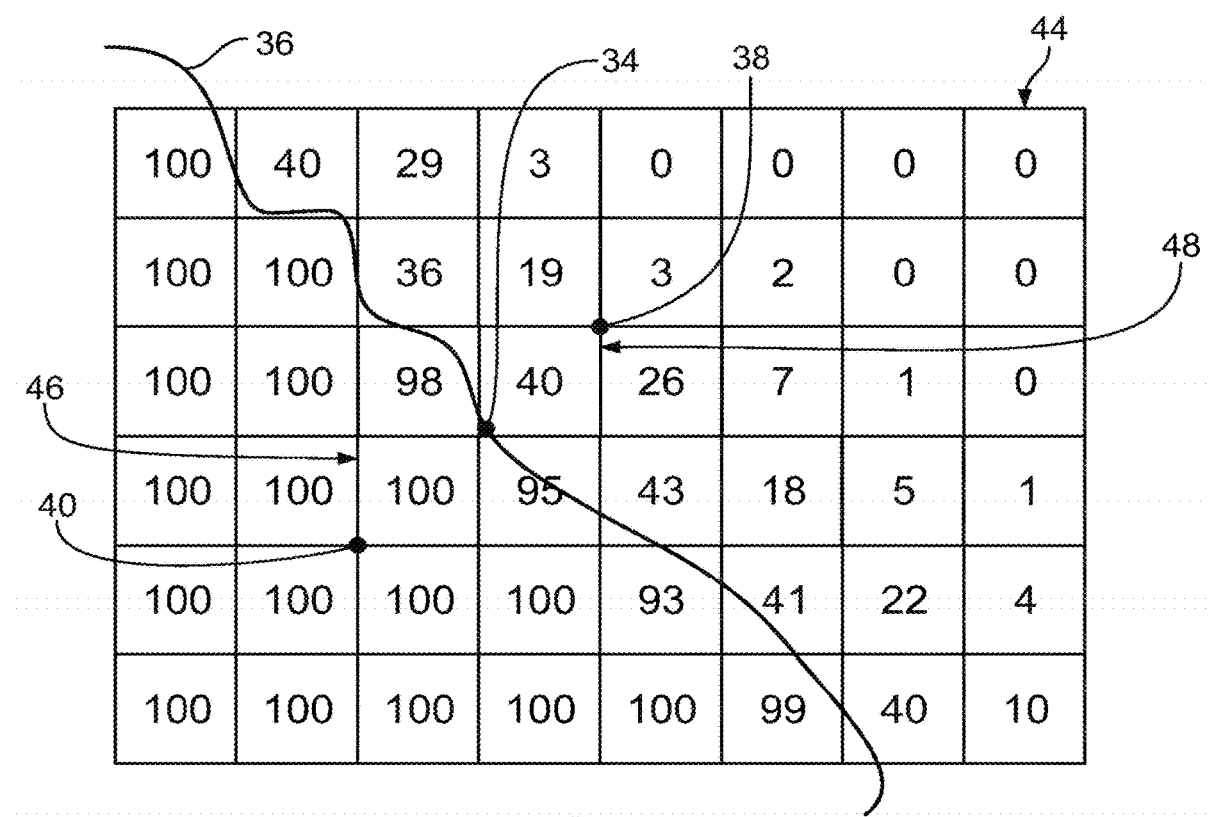
FIG. 5 shows illustrative grayscale data for patient imaging data used to calculate gradients at a point on a surface of a bone model.

A planar slice of image data (e.g., MRI image data) is represented as a grayscale grid 44 shown in FIG. 5. The planar slice may be taken along any suitable plane through the bone model such as the sagittal, coronal, or oblique plane, or any other suitable plane. The grayscale grid 44 shows the signal intensity at each point along the planar slice. For example, a signal intensity of 100 may represent a bright object in the MRI image data, which may correspond to fluids or cartilage. A signal intensity of 0 may represent a darker object in the MRI image, which may correspond to cortical bone. The planar slice shown in FIG. 5 is segmented by line 36 to define a boundary between a bone and other tissue. To compute gradients using the grayscale grid 44, a signal intensity value is determined along the line 36 and compared with a signal intensity value that lies in a direction away from the line 36. For example, point 34 corresponds to a corner of the grayscale grid 44 between image segments represented by blocks 46 and 48. When the point 34 is analyzed to calculate gradients, the points 38 and 40 used for analysis lie on opposite corners of boxes 46 and 48. The underlying grayscale values shown in the grid 44 are then used to calculate the gradients from point 34 to determine the accuracy of the location of modeled surface 36.

The grayscale values in the boxes 46 and 48 of the grid 44 indicate the color changes in the region of point 34 in directions normal to the surface 36. In particular, the point 34 lies between a grayscale value of 40 on the outside of the surface 36 and a grayscale of 100 on the inside of the surface 36. When gradients are calculated between point 34 and each of points 38 and 40, a difference in grayscale will be apparent. For example, the point 34 may be located at a grayscale of 70, while the point 38 may be at a grayscale of 20. Likewise, the point 40 may be at a grayscale of 100. These values are exemplary, and any other values may be the values of the grayscales in the grid 44. When the gradient is calculated from points 34 to 38, a significant difference will be apparent, as the difference between a grayscale of about 70 and a grayscale of about 20 produces a gradient of around 50. Likewise, moving into the bone, the grayscale difference between points 34 and 40 may be about 30.

The imaging data in the grid 44 and the gradients calculated around point 34 indicate that the surface 36 is at an accurate location within the imaging data. Appreciable grayscale gradients towards both the outside and the inside of the surface 36 indicate that the point 34 is located at an adequate transition point between the bone and surrounding soft tissue. Thus, when the model 26 in FIG. 3 is displayed to the operator, an indicator is graphically placed at the point 34 to notify the operator that the gradient analysis has determined that the surface 36 is accurately located at that point.

Figure 6:
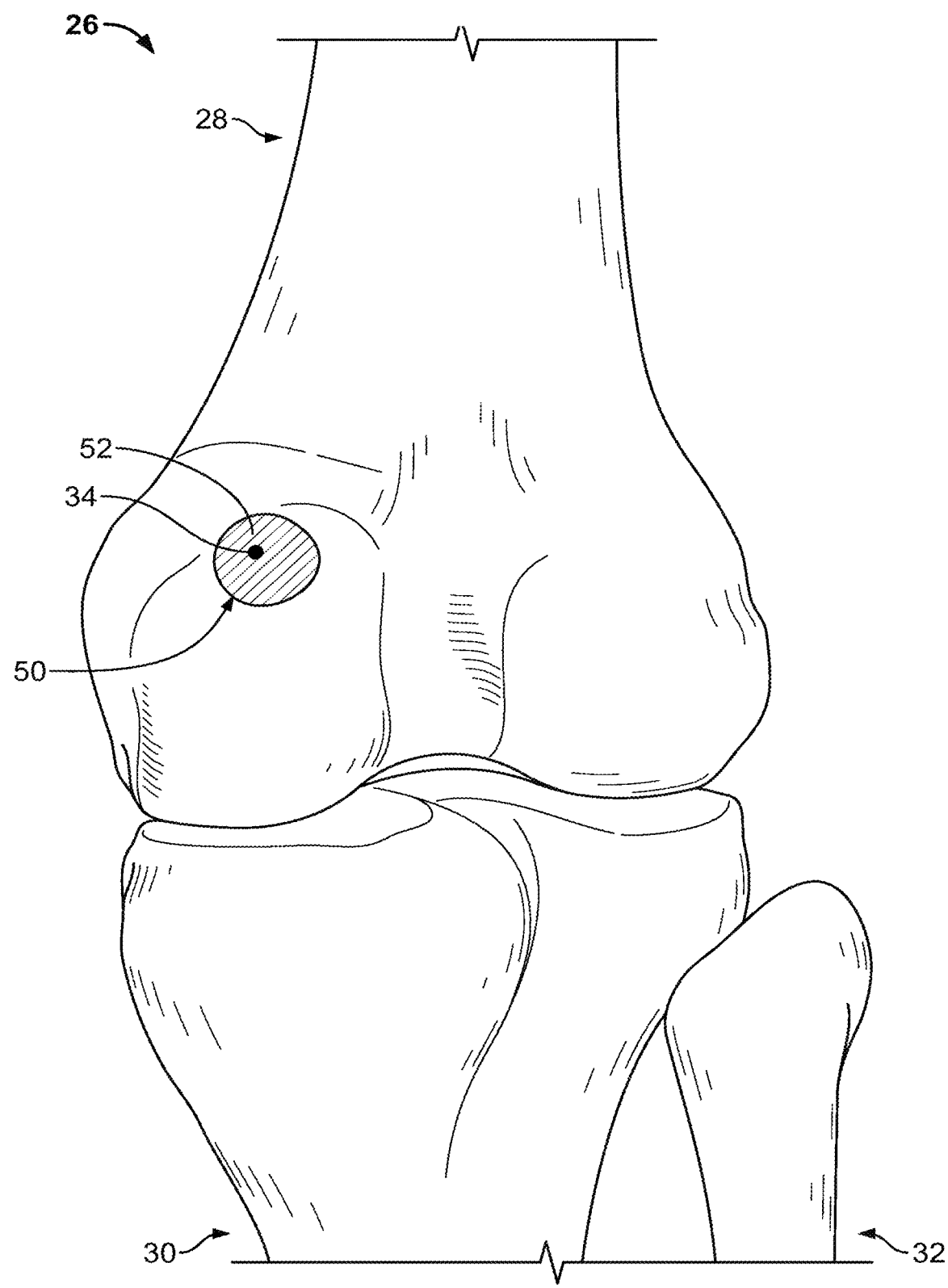
FIG. 6 shows a knee bone model with an area indicated as an accurate estimation based on the grayscale values shown in FIG. 5.

FIG. 6 shows the bone model 26 displayed with an indicator 52 in a region 50 of the bone that includes the point 34. Indicator 52 is a shading or coloring that corresponds to an indication of accuracy based on the determination that the gradients calculated from the imaging data in FIG. 5 at point 34 meet or exceed a set gradient threshold and that the surface at point 34 is accurately placed. The inclusion of the indicator 52 at the region 50 gives the operator a quick and easily interpreted indication that the model 26 maps closely to the imaging data at and around point 34. This information can be used by the operator to rely on the model 26 if a surgical implant or surgical guide is designed around the area of the point 34. The indicator 52 also gives the operator a clear, point-by-point indication of the accuracy of the model over the surface of the bone, rather than an overall estimate, such as a standard deviation or confidence value, that may vary from one region of the bone to the other.

Figure 7:
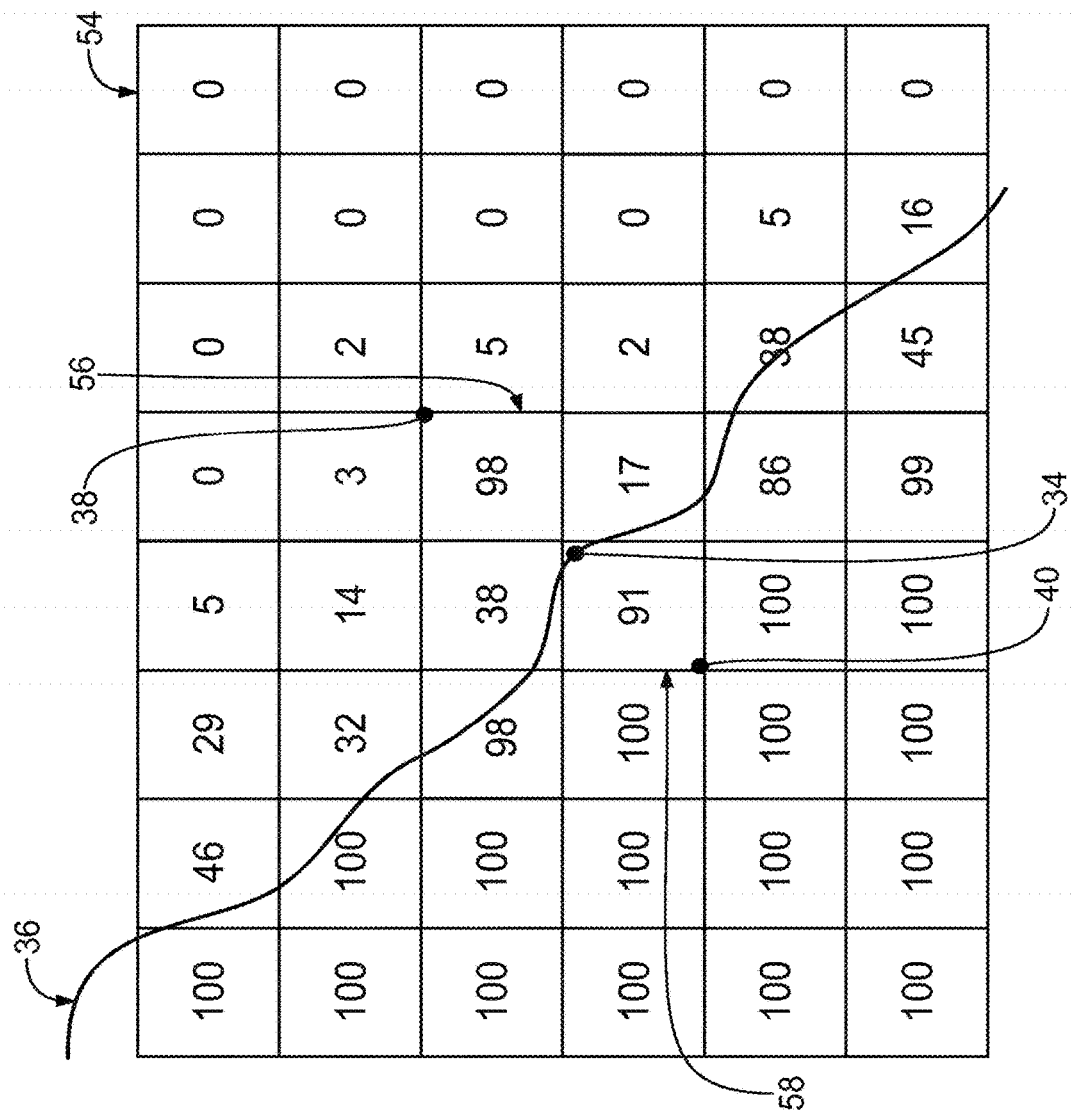
FIG. 7 shows illustrative grayscale values for patient imaging data used to calculate gradients at a point on a surface of a bone model.

In some cases, comparison of a modeled bone with the underlying imaging data may determine that the bone surface and bone surface contours are not as accurately placed as they are in FIGS. 5 and 6. The grayscale grid 54, shown co-registered with the surface 36 in FIG. 7, is one example of such a situation. In FIG. 7, point 34 is shown with the gradient points 38 and 40 as in FIG. 5, but with a new grayscale grid 54. In this example, the gradient points 38 and 40 are placed at opposite corners of image segment boxes 56 and 58, respectively. As opposed to the grid 44 shown in FIG. 5, the gradient from inside the surface 36 to outside the surface is not as significant in the grid 54. In particular, the inside of the surface 36 exhibits the expected high grayscale values, with the value 91 in the image segment block 58. The area outside the bone, however, does not exhibit the low grayscale values that would be expected if the surface 36 were accurately placed. For example, image block 56 has a grayscale value of 98, which is higher than the inner bone value of 91 in block 58. When gradients are calculated from point 34, the lack of appreciable gradient between the points 40 and 38 indicates that the surface 36 is not an accurate representation of the patient's anatomy.

When the imaging data grid 54 is co-registered with the surface 36, a processing system calculates a gradient between points 34 and 40 and between points 34 and 38. Because of the similarity in the grayscale values of blocks 56 and 58, neither of these two gradients will signal an appreciable change around point 34. When the two gradients are compared to thresholds, the resulting indication will be that neither gradient meets a threshold, and thus the surface 36 is not accurately placed. In this case, the model is provided to a user with a warning that data in the area of point 34 may not be reliable and that the surface 36 of the model 26 deviates from the patient anatomy that is indicated by the co-registered imaging data grid 54.

Figure 8:
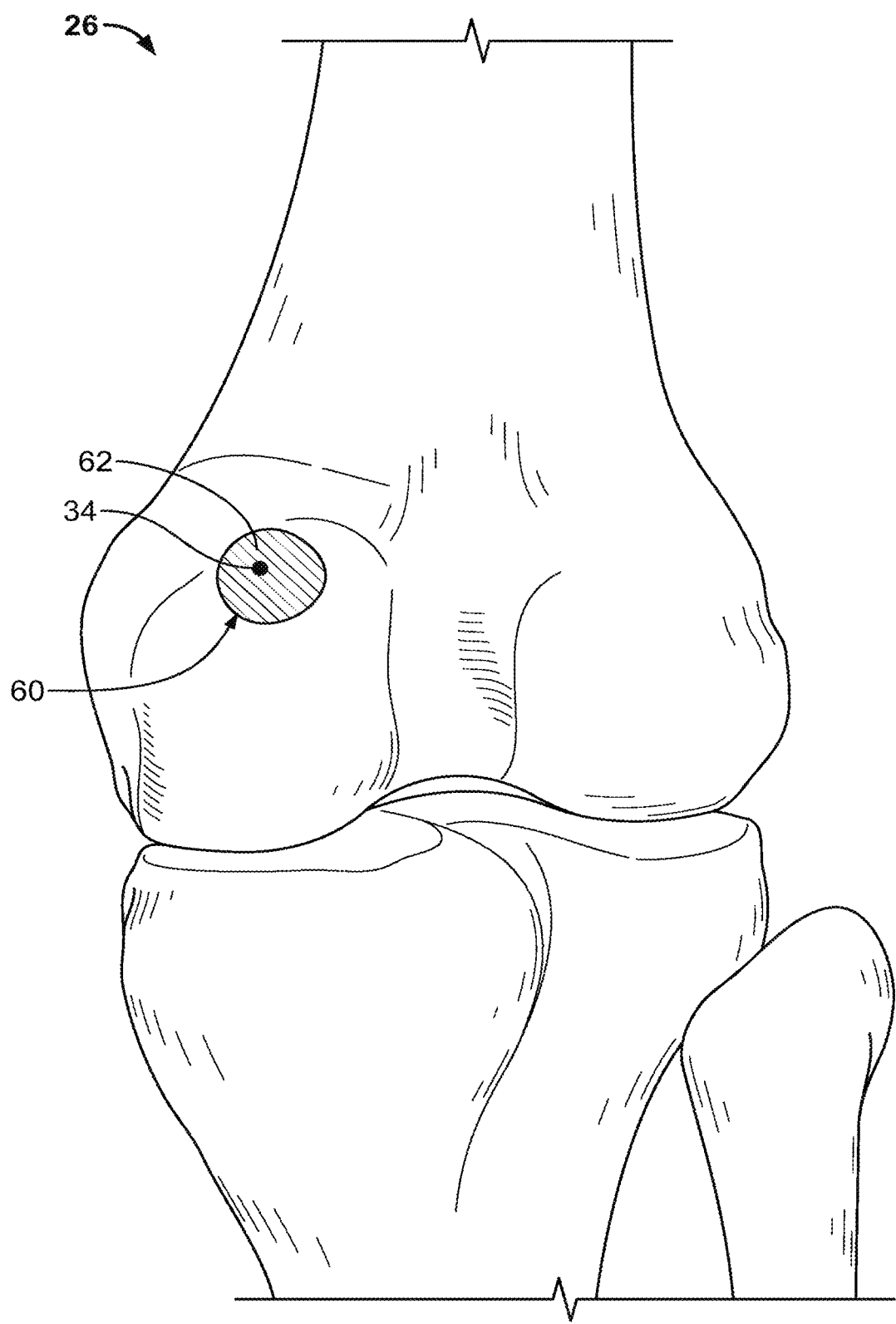
FIG. 8 shows a knee bone model with an area indicated as an inaccurate estimation based on the gray scale values shown in FIG. 7.

FIG. 8 shows the model 26 with an indicator 62 displayed in a region 60 around point 34. The indicator 62 is a visual flag for the user that the model in the area of point 34 has been determined to deviate from the patient's anatomy and thus may not be reliable. Indicator 62 may be a shading or color associated with inaccurate data. For example, indicator 62 may be a red color to indicate a warning to the user and distinguish the region 60 from the surrounding regions of model 26 in which the data has been determined to be accurate. By providing the indicator 62 in region 60 overlaid onto the bone model 26 itself, the user is provided with a single model that gives an estimation of the bone, as well as an indication where the model 26 may not be entirely reliable. This is a useful indication for the user, particularly in designing a surgery involving the region 60 or a device configured to contact the bone in the area around point 34.

Figure 9:
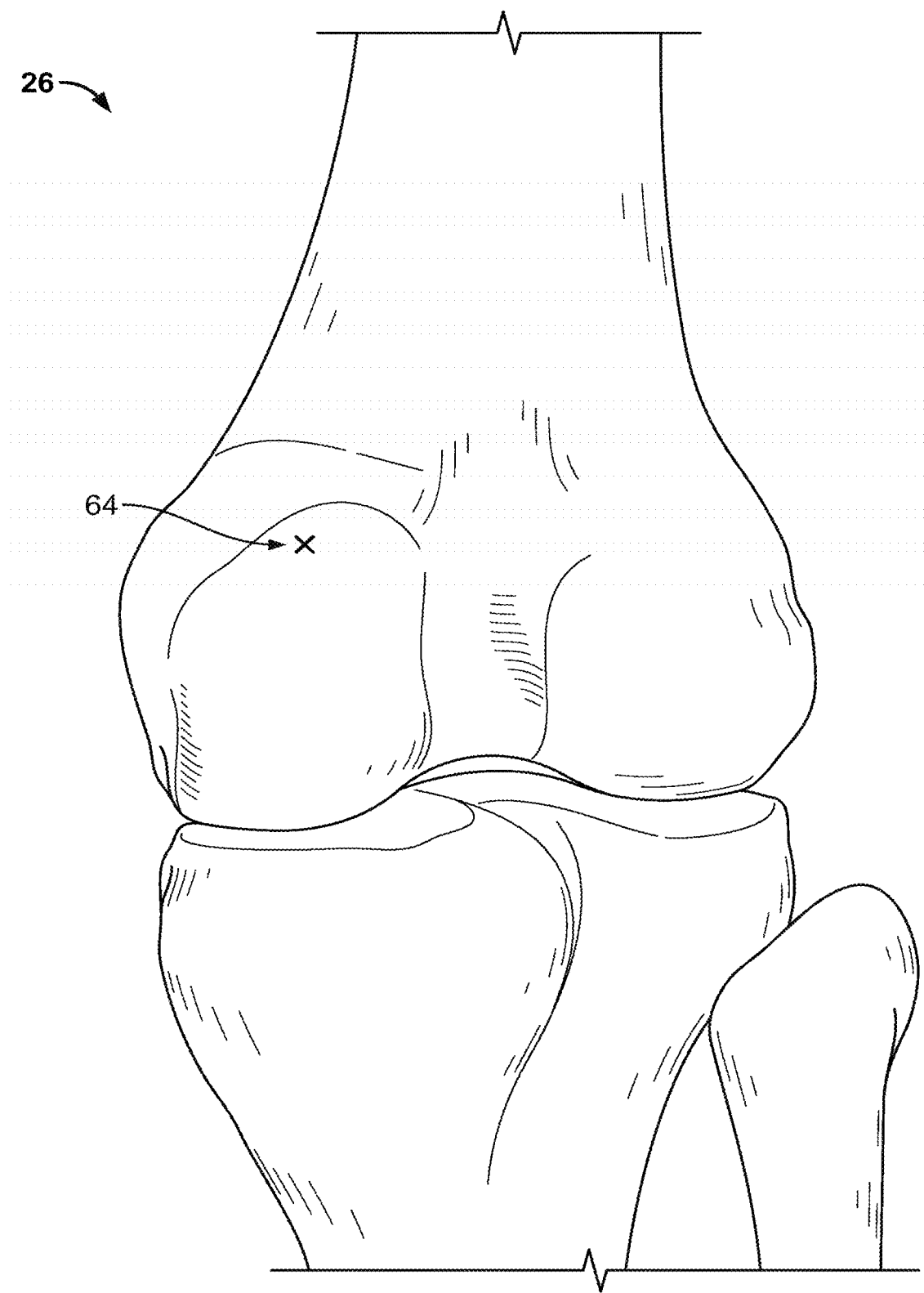
FIG. 9 shows an illustrative knee bone model with a point on the model marked with a graphical indicator based on the grayscale values shown in FIG. 7.

In addition to providing a regional shading, such as that shown in FIG. 8, a graphical indicator may be displayed on a model to indicate potentially inaccurate areas of the bone model 26. FIG. 9 shows an example of a graphical indicator 64 displayed on the model 26, rather than a shading like the indicator 62 of FIG. 8. In addition to point 34, other points on the surface of the bone model 26 may be analyzed to further determine whether gradients are present around the estimated surface of the bone model 26. For each point at which the calculated gradients do not meet a set threshold, additional indicators, like the graphical indicator 64, may be displayed. Though the graphical indicator 64 is shown as an X shape on the surface of the model 26, any suitable indicator or shape that provides the user with a visual cue that the point has failed the gradient threshold test would suffice. Once a substantial portion of the points on the surface of the model 26 are analyzed and graphical indicators are placed on the model, the user is provided with a single display that includes the model and a map of problem areas in which indicators such as the graphical indicator 64 are more highly concentrated than other areas of the model 26.

Figure 10:
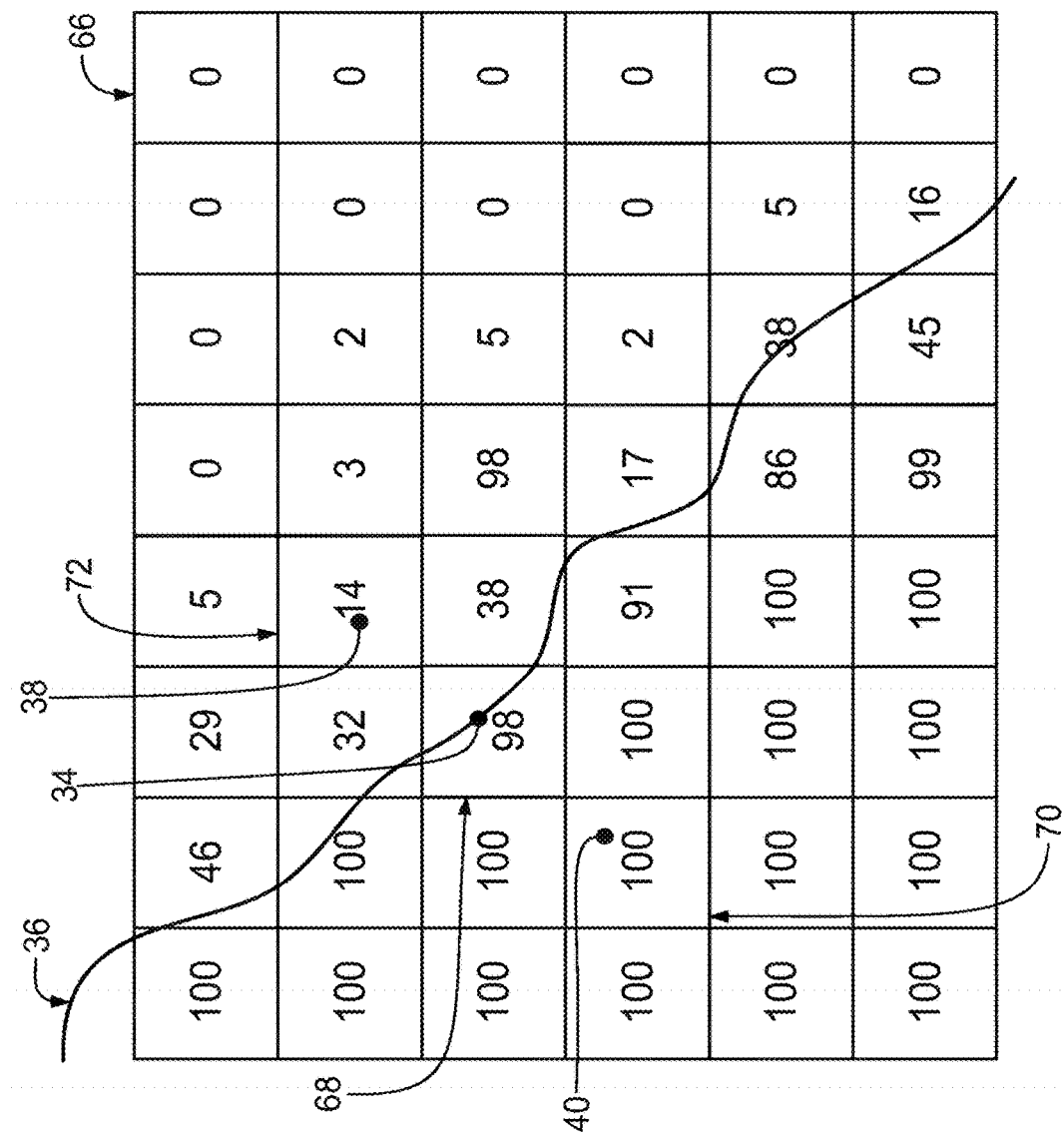
FIG. 10 shows illustrative grayscale values for patient imaging data used to calculate gradients at a point on a surface of a bone model.

For some models, when a bone surface is co-registered with underlying imaging data, a gradient may be present in only one of the two directions normal to the model surface. FIG. 10 shows an example of this situation, in which the surface 36 is co-registered with the grayscale grid 66 of imaging data. As shown in the grid 66, the point 34 is located within an image segment block 68, having a grayscale value of 98. The point 40 located within the bone is in block 70, which has a grayscale value of 100, and a point 38 is located outside of the bone in block 72, which has a grayscale value of 14. In this situation, when gradients are calculated from point 34 there will be an appreciably large gradient towards the outside of the bone to point 38, but only a relatively small gradient toward the inside of the bone to point 40. For example, from the grayscale values indicated in each block, the difference between point 34 and point 40 is about 2, and the difference between point 34 and point 38 is about 84. In this situation, only one of the two gradients, the gradient towards point 38, may meet set thresholds and indicate that the surface 36 is near the actual patient bone surface indicated by the imaging data, but may not be optimally placed within that data.

In the example shown in FIG. 10, there are various approaches for displaying the model to the user with an indication that only one of the gradients at point 34 meets a set threshold. In a case in which only one threshold is checked at each point, for example all thresholds into the bone or all thresholds out of the bone, this result would be displayed as either an accurate or an inaccurate point. For example, in a model in which only inner gradients were taken, the point 34 in FIG. 10 would be displayed as an inaccurate point because there is only a relatively small gradient between point 34 and point 40. By contrast, in a system that analyzes only outside gradients, the point 34 would be displayed as an accurate point, as the gradient between point 34 and point 38 is relatively large.

Alternatively, models that take into account both inner and outer gradients may process the difference shown in FIG. 10 in a number of different ways. A rule may be implemented that points are only shown as accurate if both an inner and an outer gradient meet a set threshold. In that case, point 34 would be shown as an inaccurate point because only one of the two gradients, the gradient outward toward point 38, meets a set threshold. Alternatively, a rule may state that the points are displayed as accurate if any one of the two gradients is determined to be accurate. For such a rule, the point 34 would be displayed as an accurate point because, although the gradient inward toward point 40 does not meet a threshold, the gradient outward from the bone surface to point 38 is a relatively large gradient and meets the threshold.

In an alternate approach, a model may make a further differentiation between points along the surface 36 for which two gradients meet a threshold, points for which neither gradient meets a threshold, and points for which only one of the two gradients meets a threshold. For example, any point on the surface 36 that meets two threshold gradients could be displayed in a first color, a point that meets only one threshold gradient could be displayed in a second color and a point that meets neither of the threshold gradients could be displayed in a third color. Further, the color in which a point is displayed if only one gradient meets the threshold may change to indicate whether it is the gradient into the bone or the gradient out from the bone that was met by the point. Thus, a model may include regions that have as many as four different colors in areas of the bone, based on the different gradient determinations.

The gradient calculations and threshold determinations described above for point 34 in the bone model may be made at points all across the surface of the bone in a three-dimensional model. For each point, a determination will be made whether or not the gradients indicate accurate or inaccurate placement of the modeled bone surface, and any points that are considered to be inaccurate will be marked in the model. After the full range of points are analyzed, a model is created that indicates a type of heat map, showing over the full area of the bone surface which areas are determined to be accurate representations and which areas deviate slightly from the underlying imaged patient anatomy. These regions are differentiated in the model and provided to the user to give a quick and efficient indication not only of overall accuracy of the model, but also relative accuracy between different areas of the model.

Figure 11:
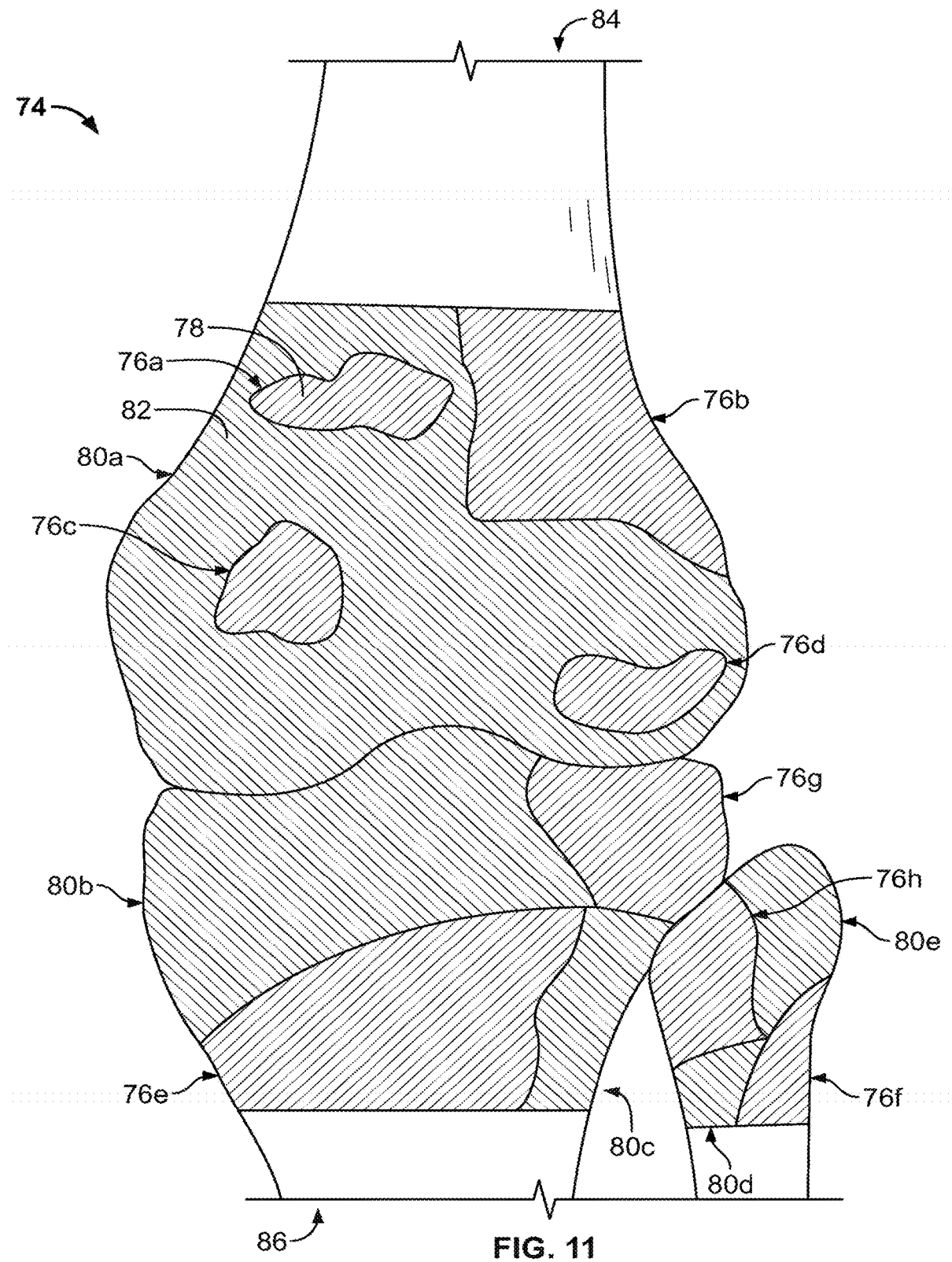
FIG. 11 shows a knee bone model with multiple areas of the model shaded to indicate gradients calculated at each point on the surface of the bone model.

FIG. 11 shows a bone model 74 with indicators placed over the surface of the bone model to signal determined accuracy compared to the underlying patient anatomy in various regions of the model 74. For example, in regions in which the points on the surface are determined to be accurately placed, for example in regions 76a-h, an indicator 78 is placed on the bone model. Indicator 78 may be a graphical indicator or may be a color or shading with the color corresponding to accurate data. In each of the areas 76a-h, a plurality of surface points have been determined to exhibit gradients that meet set thresholds, and the modeled representations of these areas are considered to be accurate. In contrast, areas in which the gradients do not meet thresholds, for example in regions 80a-e, a different indicator 82 is displayed. The indicator 82 may be a second type of graphical indicator or a second color or shading that indicates to the user that data in those areas of the model 74 deviates slightly from the patient's anatomy.

In some implementations, the model 74 includes additional indicators on top of the indicators 78 and 82 or additional colors. For example, in cases where both inside and outside gradients are tracked and a different color is displayed when only one gradient is met, a third color is included in those areas of the model 74. Furthermore, if the one gradient system differentiates between whether the inner or outer gradient is met, four different types of indicated regions are present in the model 74 if all four gradient types are present.

The model 74 displayed to the user provides a quick snapshot not only of the patient's anatomy, but of areas of that anatomy in which the model may or may not be as reliable as other areas. This snapshot is useful for a user, for example if the model 74 is predominantly one indicator or one color. Depending on the indicator, such model would tell the user that the modeled anatomy is either highly accurate or mostly unreliable for presurgical planning purposes. If the indicators signal an inaccurate model, the user may wish to further process the data or create a new model before proceeding with surgical planning. In addition, if certain areas of the anatomy in the model 74 are critical for the surgeon's planning, for example the interface between the femur 84 and the tibia 86 for planning an articulating orthopedic joint implant, then the user can focus on those areas to decide whether the shadings indicate that the critical areas are reliable or unreliable in the model.

Figure 12:
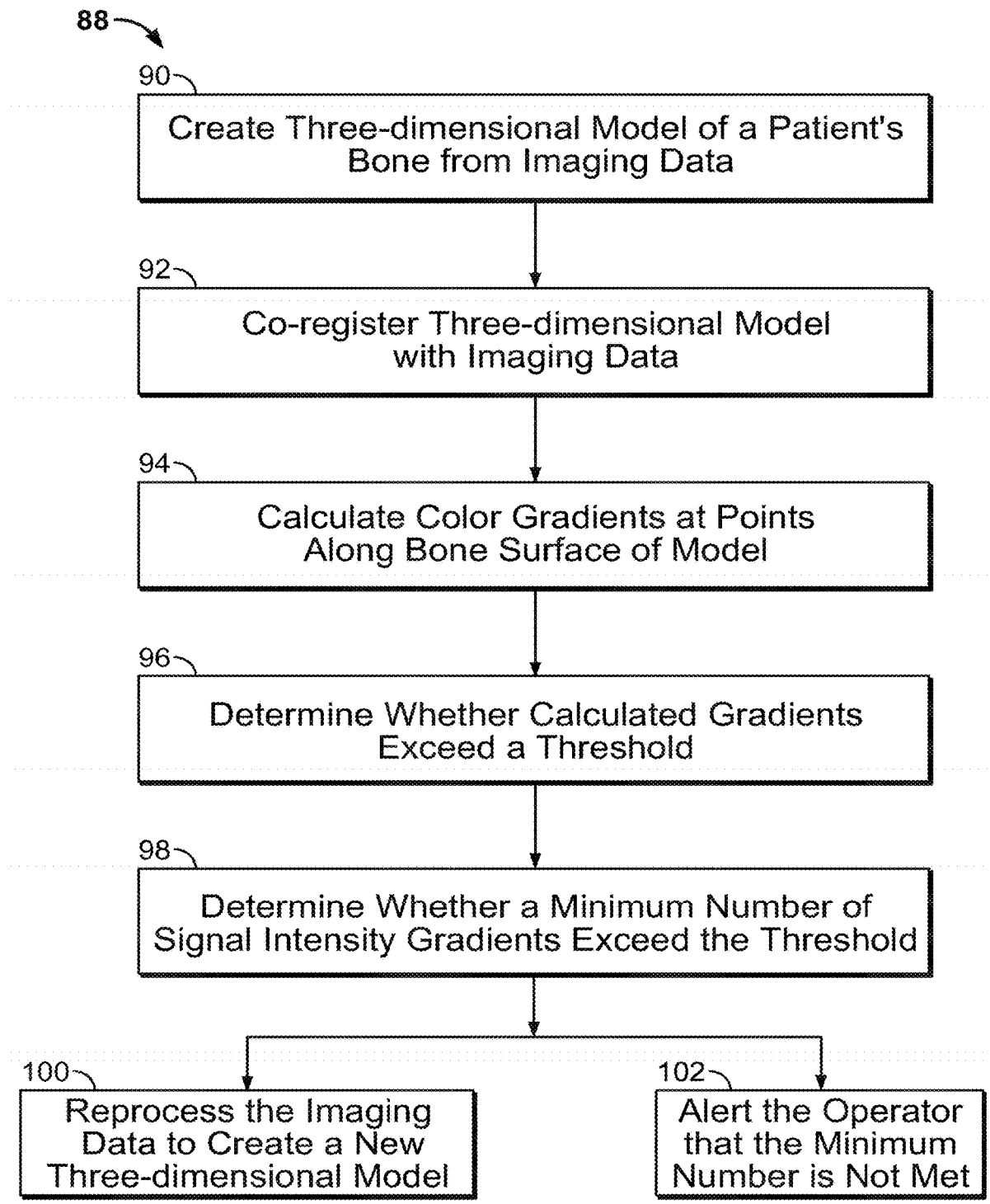
FIG. 12 shows an illustrative process for processing imaging data in a patient bone model when a minimum number of signal intensity gradients do not exceed a set threshold.

In addition to displaying a model to a user with an overlaid indicator of the accuracy of the model in various areas, the approach disclosed herein may analyze the accuracy of each point to make a determination of the overall accuracy of the displayed model. In such an implementation, the determination may be used to decide whether or not the model is suitable for the operator's purposes. FIG. 12 shows a method 88 for making such a determination. The method 88 begins with creating a three-dimensional model in step 90, co-registering a three-dimensional model with imaging data in step 92, calculating gradients at points along the surface of the model in step 94, and determining whether the calculated gradients exceed thresholds in step 96. These steps 90-96 may correspond substantially to the processes described above with respect to steps 14-20 in the method 12 of FIG. 2.

After the threshold determination is made in step 96, the number of points at which gradients were determined to exceed the accuracy thresholds is evaluated at step 98. This evaluation provides an overall understanding of the accuracy of the model as the more accurate the model is, the greater the number of points that will be counted at step 98. In some implementations, that number of gradients meeting their respective thresholds is compared to a minimum number to determine if the minimum number of acceptable gradients is met. If this minimum number is met, the system determines that the model is sufficiently accurate. If the number is not met, the system determines that the model is not adequately reliable.

If a minimum number of gradients exceeding the threshold is not met, the system provides one of two optional steps. Either of these steps or both may be implemented in a given system. First, at step 100, after the system has made a determination that the minimum number is not met and the model created at step 90 is not sufficiently accurate for the operator's purposes, the original imaging data is reprocessed to create a new three-dimensional model for the operator's purposes. This new model may then re-enter the method 88 at step 92 to make a new determination of whether the revised model is suitable for the operator's purposes.

The re-processing that occurs at step 100 may include modeling the data based on a different transformation, a different algorithm, re-segmenting some or all of the image data, a different filter or an otherwise different processing approach than was used to create the original model in step 90. Once the new model is created and passes through the method 88, if a determination is made at a step 98 for the second model that the minimum number is met, then the model is accepted. If the minimum number again fails at step 98, the second model will again enter one or both of steps 100 and 102.

As an alternative or an addition to step 100, at step 102 the system provides the user with an alert that the minimum number of accurate gradient points was not met at step 98 of the method 88. In the case where step 100 is carried out, the alert presented at step 102 notifies the user that the minimum number was not met and that a second three-dimensional model is being created and evaluated. Alternatively, if step 100 does not automatically reprocess the data, the alert provided to the operator at step 102 may provide multiple options, including an option to reprocess the data and create a new model. The options presented to the user at step 102 may also include selections of different algorithms or other characteristics and variables that are used to create the model, or may include an option for the user to accept the model as is and continue with the pre-surgical planning using the flawed model.

Figure 19:
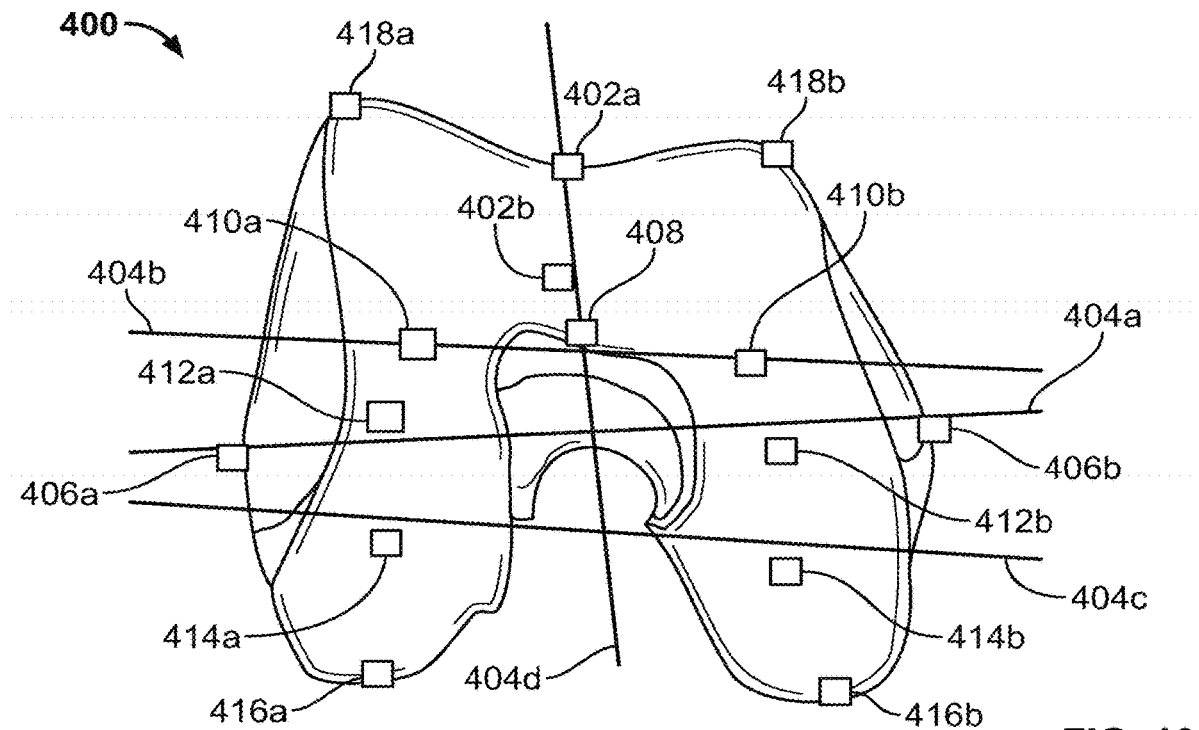
FIG. 19 shows an illustrative femur with exemplary anatomical landmarks marked.
Figure 20:
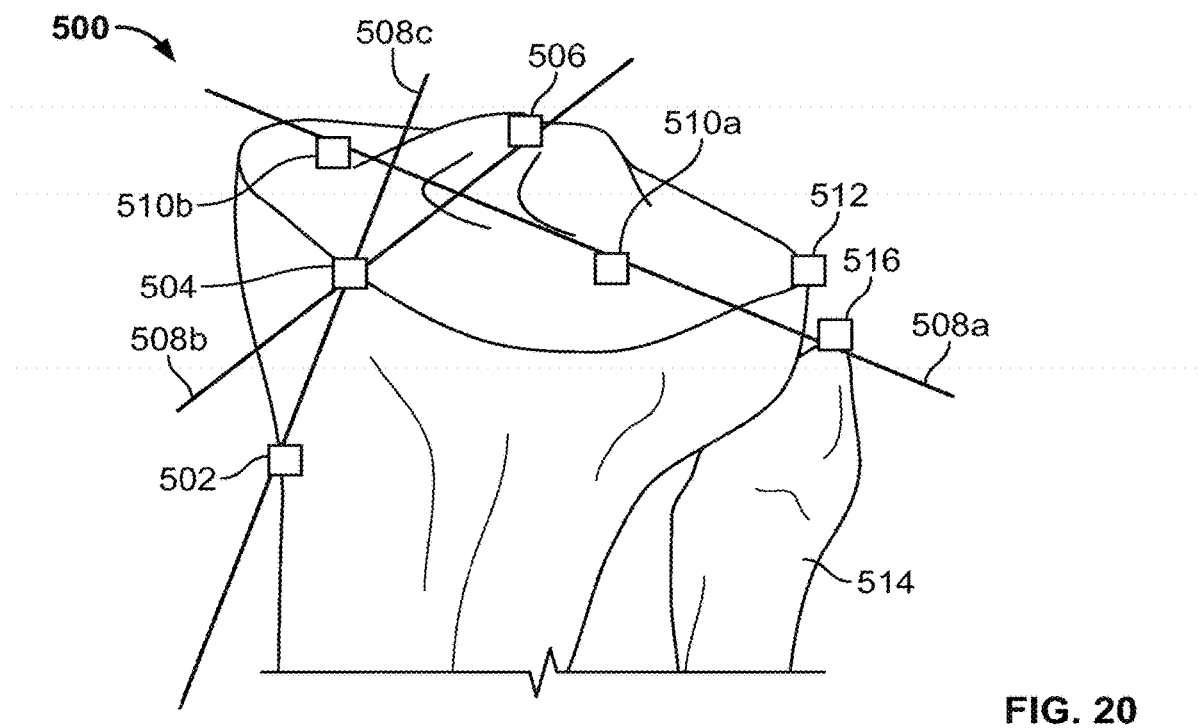
FIG. 20 shows an illustrative tibia with exemplary anatomical landmarks marked.

In cases where the operator is more interested in bone anatomy in some regions than others for a given operator's purposes, the comparison of the number of gradients that meet a threshold and a minimum number for example, the comparison carried out at step 98 of method 88, may be made with weightings applied to these points of interest in the bone model. For example, in an application in which a patient-specific implant is designed for an articular interface in the patient's knee, the areas near that articular interface between the tibia and the femur may be weighted as points of interest that are more important data points. In another example, in an application in which a patient-specific surgical guide is designed to guide the resection of a bone, the areas of the bone near where the surgical guide will contact may be weighted as points of interest that are more important data points. FIG. 19 shows an illustrative femur 400 with exemplary anatomical landmarks marked. Points that may be of interest when designing a patient specific implant or surgical guide for the femur include, for example: upper anterior portion 402a, lower anterior portion 402b, Whiteside's line 404d, lateral epicondyle 406a, medial epicondyle 406b, transepicondylar axis 404a, sulcus point 408, distal lateral condyle 410a, distal medial condyle 410b, distal condylar axis 404b, lateral condyle center of mass 412a, medial condyle center of mass 412b, posterolateral arc center 414a, posteromedial arc center 414b, posterior arc center axis 404c, posterolateral condyle 416a, posteromedial condyle 416b, distal medial-lateral condyle axis 404b, anterolateral condyle 418a, and anteromedial condyle 418b, although it will be understood that any other suitable points of interest may be designated. FIG. 20 shows an illustrative tibia 500 with exemplary anatomical landmarks marked. Points that may be of interest when designing a patient specific implant or surgical guide for the tibia 500 include, for example: tibial tuberosity 502, anterior tibial plateau 504, apex of intercondylar eminience 506, tibial A-P axis 508b, lateral sulcus point 510a, medial sulcus point 510b, posterolateral tibial plateau 512, tibial M-L axis 508a, and axis 508c connecting the tibial tuberosity 502 with the anterior tibial plateau 504, although it will be understood that any other suitable points of interest may be designated. Shown on the fibula 514 is the fibular head crest 516.

Figure 13:
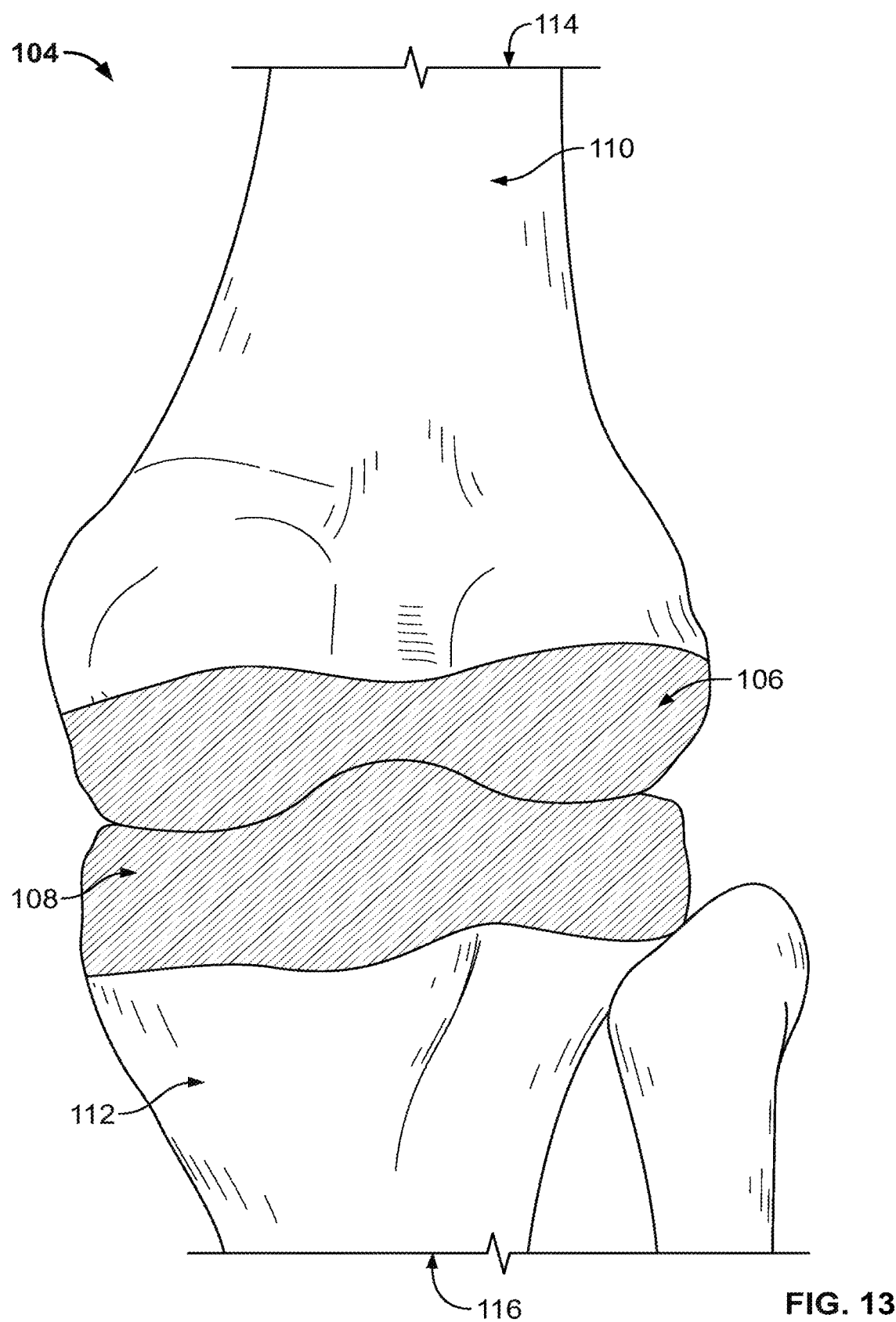
FIG. 13 shows an illustrative knee bone model with areas of the bone shaded to indicate points of interest of the anatomy.

FIG. 13 shows a bone model 104 of a knee joint including femur 114 and tibia 116 used to design a patient-specific implant or surgical guide for the articular surface at the knee. Included in the model 104 is a shaded region 106 on the distal end of the femur and a shaded region 108 on the proximal end of the tibia. These shaded areas 106 and 108 are areas used for designing an articular implant between the bones 114 and 116. Thus, the shaded areas 106 and 108 are of more interest for the design of the patient-matched implant than the non-shaded area 110 of the femur 114 and the non-shaded area 112 of the tibia 116. In order to account for the importance of the shaded areas 106 and 108, the data points for which gradients are calculated that fall within those shaded regions are weighted by a factor, for example, two or three or more, when the determination of whether a minimum number of gradients have met the threshold is made, for example in step 98 of method 88. By counting the points within the shaded areas 106 and 108 multiple times compared to the non-shaded regions, the determination of accuracy stresses the importance of the areas of the bone model 104 from which the implants will be designed. The shaded areas 106 and 108 may also be used as areas of interest when designing patient-matched surgical guides that guide the resection of the bone in preparation for an implant.

The accuracy indications and overlays discussed above using gradients at the modeled bone surface provide an operator with a labeled model that indicates potential weaknesses of the model and identifies problem areas in the modeled bone. Similar indications can be calculated and provided using metrics other than gradient, depending on the type of modeling or surgical approach used. Another example of such a metric is curvature along the surface of the modeled bone. A patient's bone may have areas in which the curvature is expected to be either concave or convex, and there may be areas of the bone where transitions between concave and convex surfaces are expected. For example, the medial and lateral condyles of a femur are expected to be convex to form the rounded articulation surface of a knee joint. The intercondylar fossa between the two condyles is normally concave, providing the recessed notch typically found on the distal end of the bone. Along a transition between the condyles and the intercondylar fossa, inflection points are expected as the surface changes from convex to concave. When this area of the bone is imaged and modeled, the surface curvature can be used to confirm that the surfaces exhibit the expected curvature and transitions, with relatively large deviations from that expected anatomy potentially indicating flaws in the modeling process.

Figure 14:
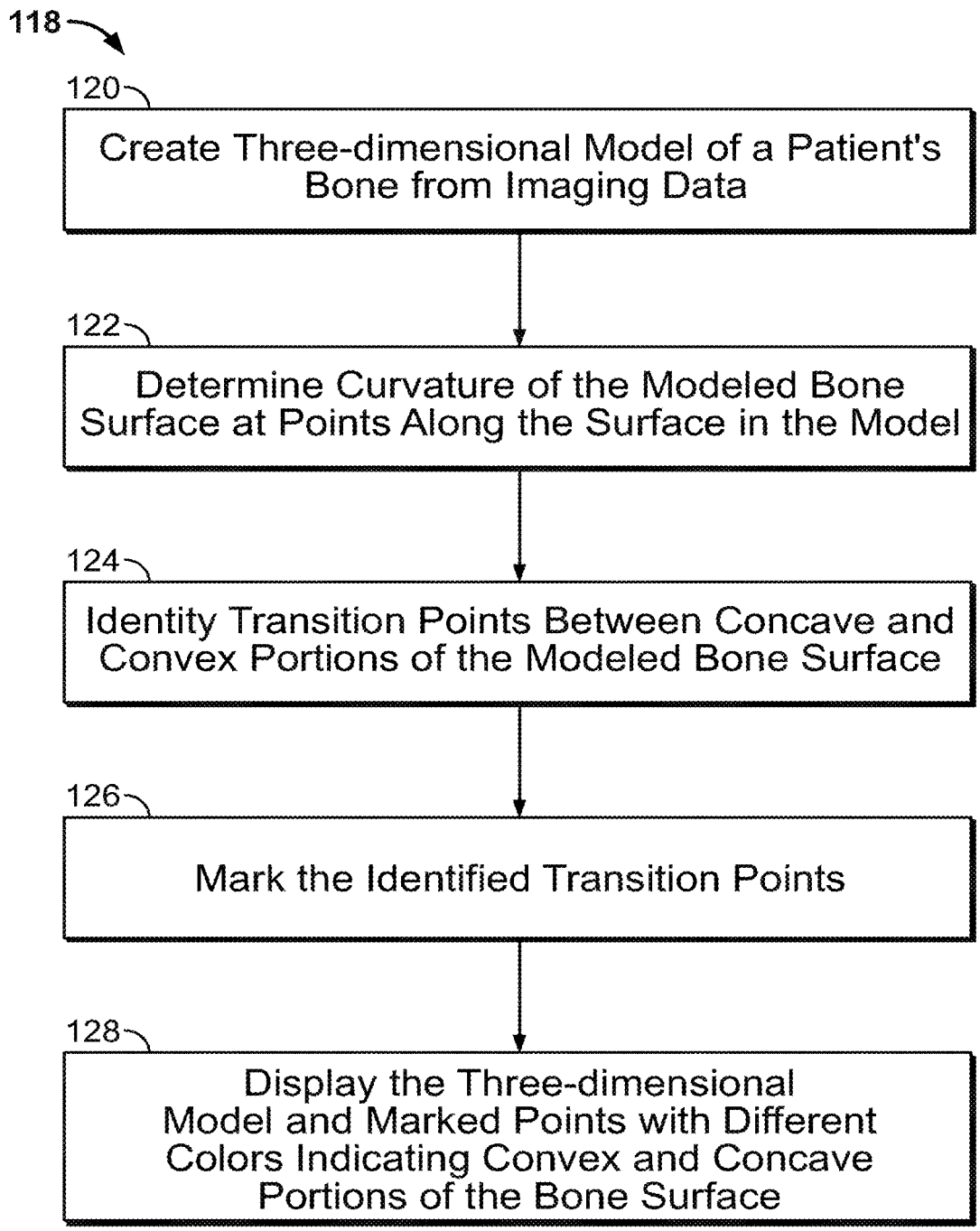
FIG. 14 shows an illustrative process for indicating transition points and curvature on a patient bone model.

FIG. 14 shows a method 118 for using bone model surface curvature analysis to analyze and indicate the accuracy of the model. The bone model is created from imaging data at step 120. This step is substantially similar to the step 6 described above in connection with FIG. 1, and the imaging data used to create the model may be obtained in an approach similar to that described above with regards to step 4 of FIG. 1. The bone model created at step 120 is analyzed at step 122 to determine the curvature of the modeled surface at a number of points along the surface of the model. In contrast to the gradient analysis discussed above, the curvature analysis operates only on the bone model itself and does not require co-registration with the underlying imaging data to perform the analysis. At each point analyzed in step 122, the model is processed to determine if the surface in the model exhibits a concave or convex curvature, and the point is marked with the determined curvature.

After points on the surface of the model across different regions of the surface are analyzed for curvature, the changes between regions can be identified. In particular, points in areas where the surface transitions from convex to concave curvature are identified at step 124 as transition points on the surface. These transition points are estimates for the inflection points in the model, and a series of inflection points may form a transition line that establishes a boundary between concave and convex regions of the model. At step 126, these determined transition points are identified in order to provide an indication to the operator where those boundaries are present in the modeled bone.

The bone model, curvature regions, and transition points are displayed for the operator at step 128. Similar to the displays described above with gradient indicators, the display provided at step 128 gives the operator a bone model with an indication of model accuracy overlaid on the modeled bone. The operator is provided with a single model that both provides the shapes and contours of the bone for surgical or implant planning and also provides indicators that may alert the operator to areas of the model that are inaccurate. If the operator discovers that many areas of the model exhibit unexpected curvature, or that transitions between curvature are in unexpected regions, then the operator may determine that the model is not adequately accurate. The operator's decision may be informed both by the standard expected characteristics of the modeled bone and by images of the particular patient's bone, for example MRI or X-ray images.

In addition to the surgeon's own analysis and determinations, the processing systems described herein may automatically analyze the determined curvatures and transition points in the model to determine inaccuracies. For example, the system may count the number of analyzed points in the model that are determined to be transition points. If that number is abnormally high, for example higher than a set minimum number, then the system may determine that there are too many transitions in the model that would not be expected for a bone that typically does not exhibit sharp transitions. The system may use that determination to automatically reprocess the underlying imaging data and provide a new model, for example by using additional smoothing algorithms to eliminate some of the unwanted transitions. The system may also alert the user that a relatively large number of transitions are present, either at the same time as automatically reprocessing the data or along with an option for the user to cause the system to perform such reprocessing. Certain areas of the bone may also be weighted when the minimum number comparison is made, for example to give more weight to transition points found in areas like the femoral condyles on which such transition points are not expected.

Figure 15:
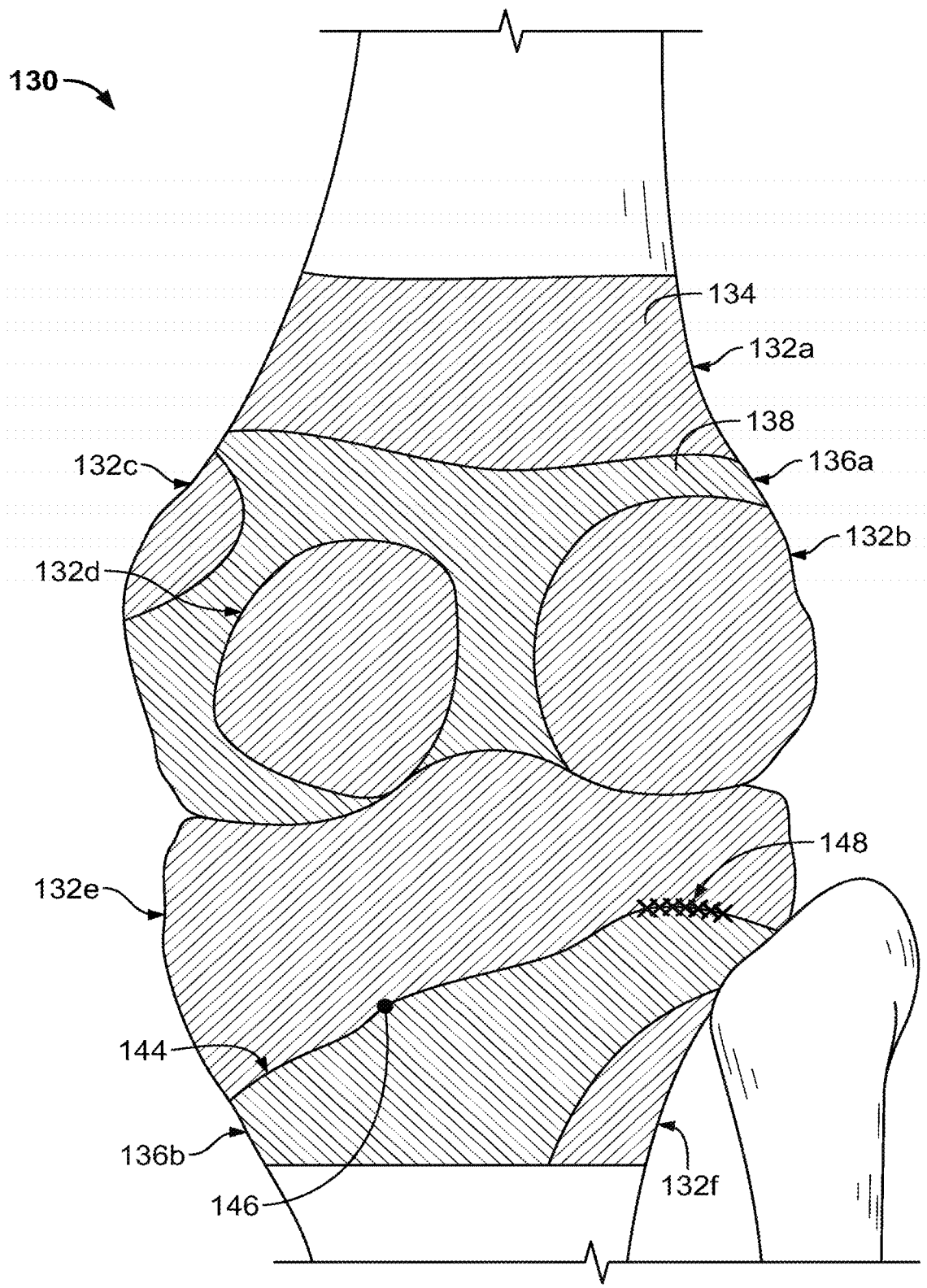
FIG. 15 shows an illustrative knee bone model with areas of the model shaded to indicate curvature.

FIG. 15 shows a bone model 130 provided to an operator with curvature and transition overlays included on the model. The model 130 includes multiple convex regions 132*a-f* each marked with an indicator 134, for example a color shading or a graphical indicator, to highlight points at which the curvature in the model surface is convex. A group of concave regions 136*a-b* are marked with a second indicator 138, for example a second color shading or second graphical indicator, to highlight points at which the curvature in the model is concave. As shown in the model 130, the concave areas appear at areas of the bone expected to be concave, such as the intercondylar fossa contained in the region 136*a*. Likewise, the convex areas of the bone appear at expected locations, for example in regions 132*b* and 132*d* on the femoral condyles. This model provides an operator with an indication that the model is accurate, as curvature indications are in line with the expected curvature of the modeled portion of the patient's anatomy.

The model 130 also includes a number of marked transition points that create transition lines between concave and convex areas, for example transition line 144 between convex region 132*e* and concave region 136*b*. The transition line 144 is formed from a plurality of points, such as point 146, at which the model analysis determines that curvature changes from concave to convex. Point 146, and other transition points in the line 144, may be displayed with an indicator different than the indicators used for convex and concave regions of the surface. For example, the line 144 may be displayed in a color different than the color used for the curved areas, or may be displayed with a graphical indicator such as the group of Xs 148 shown in FIG. 15 for points on the line 144.

Figure 16:
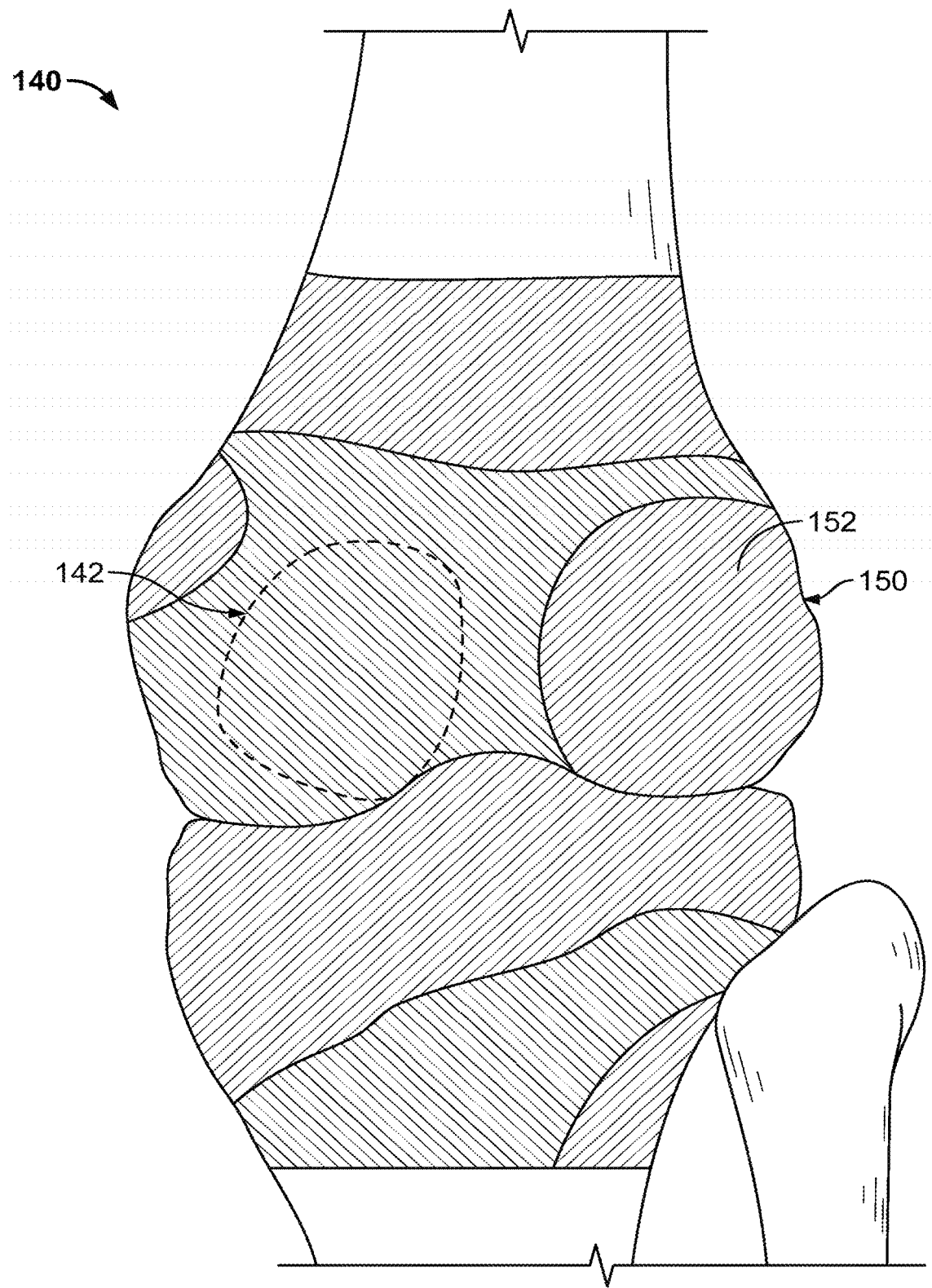
FIG. 16 shows an illustrative knee bone model with areas of the model shaded to indicate curvature.

By providing the curvature and transitions on the model 130, the model allows an operator to make quick judgments of the accuracy of the models. If an area known to have one curvature is not marked as such on the model, a red flag may be raised to question the data processing that produced the model. For example, FIG. 16 shows a bone model 140 in which a condylar region 142 outlined with a dotted line is marked with an indicator 154, such as a color shading or a graphical indicator, that indicates concave curvature. In this bone model, the condyles are expected to exhibit convex curvature, for example like the region 150 marked with convex indicator 152. When the operator views the model 140 and sees the concave indicator 154 in region 142, it is a flag that the model 140 likely contains inaccuracies in that region. The operator may decide to reject the model and reprocess imaging data, particularly if the region 142 is important to the surgery or device design for which the model 140 is being used.

Figure 17:
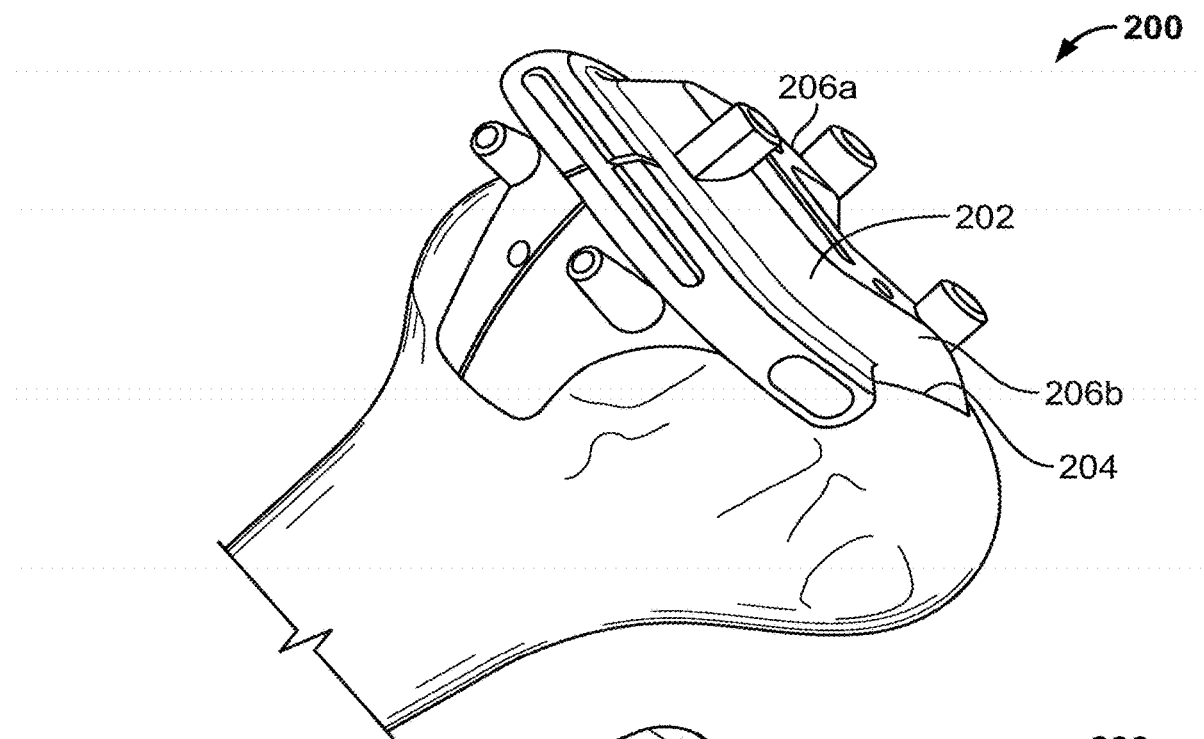
FIG. 17 shows an illustrative femur model with a patient-matched femoral cutting guide.

FIG. 17 shows an illustrative femur model 200 with a patient-matched femoral cutting guide 202 according to certain embodiments. The patient-matched femoral cutting guide 202 is designed using the systems and methods described herein. In particular, the femoral cutting guide 202 includes an inner surface 204 that is designed to include contours that match the contours of a surface of the femur model 200. As shown in FIG. 17, the patient-matched femoral cutting guide 202 closely conforms to the trochlear groove of the femur model 200 and includes patient-matched arms 206a and 206b that extend around the posterior end of the medial and lateral condyles. The accuracy of the femur model 200 is important to ensure that the inner surface 204 of the patient-matched femoral cutting guide 202 accurately matches the patient's bone. If the patient-matched femoral cutting guide does not match the patient's bone due to, for example, errors in the segmentation of the image data (e.g., MRI image data), complications may occur during surgery. When determining if errors are present in the femur model 200, portions of the femur model 200 may be weighted more than others. For example, portions of the femur that are in direct contact with the patient-matched femoral cutting guide 202, such as inner surface 204, may be weighted relatively more than areas where the femoral cutting guide 202 does not contact the femur model 200.

Figure 18:
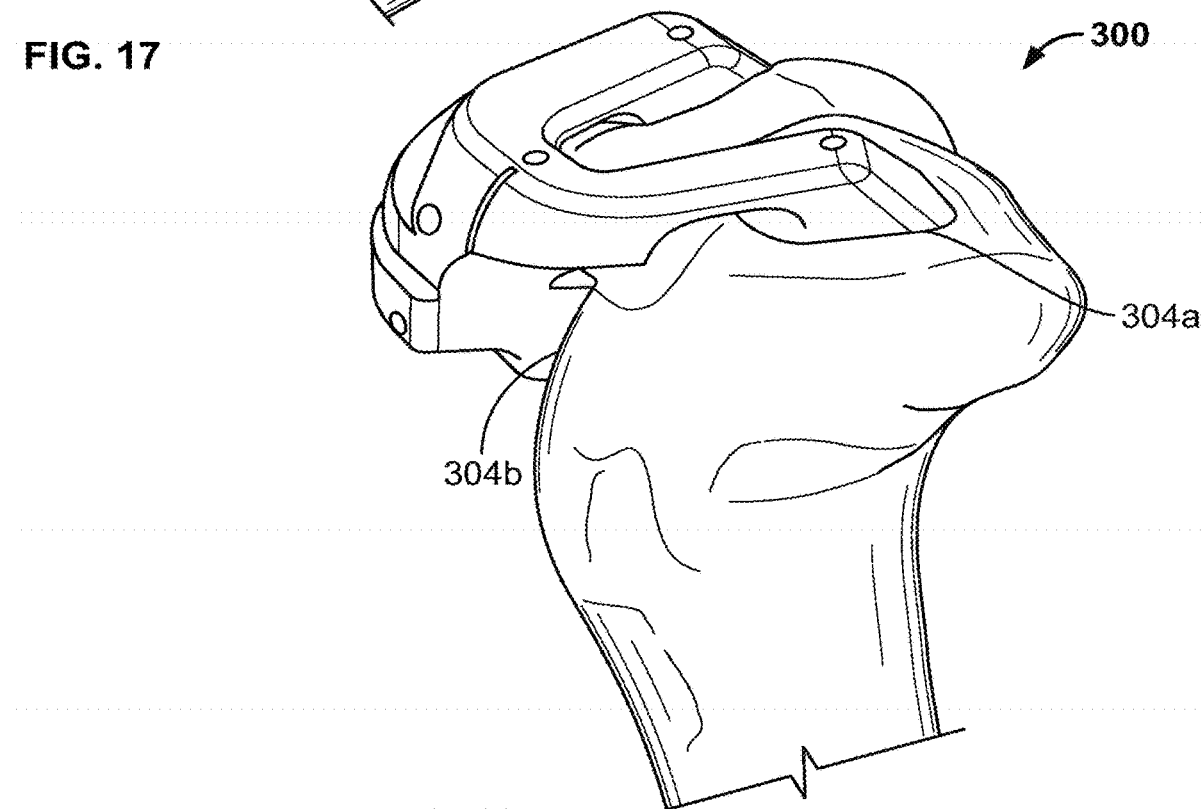
FIG. 18 shows an illustrative tibial model with a patient-matched tibial cutting guide.

FIG. 18 shows an illustrative tibial model 300 with a patient-matched tibial cutting guide 302 according to certain embodiments. The patient-matched tibial cutting guide 302 is designed using the systems and methods described herein. In particular, the tibial cutting guide 302 includes inner surfaces 304a and 304b that are designed to include contours that match the contours of a surface of the tibial model 300. The accuracy of the tibial model 300 is important to ensure that the inner surfaces 304a and 304b of the patient-matched tibial cutting guide 302 accurately matches the patient's bone. If the patient-matched tibial cutting guide does not match the patient's bone due to, for example, errors in the segmentation of the image data (e.g., MRI image data), complications may occur during surgery. When determining if errors are present in the tibial model 300, portions of the tibial model 300 may be weighted more than others. For example, portions of the tibia that are in direct contact with the patient-matched tibial cutting guide 302, such as inner surfaces 304a and 304b, may be weighted relatively more than areas where the tibial cutting guide 302 does not contact the tibial model 300.

Example Embodiments

A1. A method for indicating accuracy of image segmentation in a patient model, the method comprising:

creating a three-dimensional bone surface model of a portion of a patient's bone from imaging data;

calculating a first signal intensity gradient between a first point on a surface of the three-dimensional model and a second point spaced from the surface along a line extending from the surface at the first point; and marking the first point on the three-dimensional model if the first gradient exceeds a first threshold.

A2. The method of A1, wherein the second point is spaced from the surface at a location outside the modeled bone.

A3. The method of A1, wherein the second point is spaced from the surface at a location within the modeled bone.

A4. The method of any of A1, further comprising calculating a second signal intensity gradient between the first point and a third point spaced from the surface along the line.

A5. The method of A4, wherein:

the second point is spaced from the surface at a location outside the modeled bone;

the third point is spaced from the surface at a location within the modeled bone;

the first gradient indicates a signal intensity change outward from the surface; and the second gradient indicates a signal intensity change inward from the surface.

A6. The method of A4 or A5, further comprising determining whether each of the first and second gradients exceeds a threshold.

A7. The method of A6, further comprising determining whether each of the first and second gradients exceeds the first threshold.

A8. The method of A6, further comprising: determining whether the first gradient exceeds the first threshold; and determining whether the second gradient exceeds a second threshold.

A9. The method of any of A6-A8, wherein marking the first point comprises marking the first point if both of the first and second gradients exceed a threshold.

A10. The method of any of A6-A8, wherein marking the first point comprises marking the first point if either one of the first and second gradients exceeds a threshold.

A11. The method of any of A6-A10, wherein marking the first point comprises displaying the first point in a first color if both of the first and second gradients exceed a threshold, displaying the first point in a second color if only one of the first and second gradients exceeds a threshold, and displaying the first point in a third color if neither of the first and second gradients exceeds a threshold.

A12. The method of A11, wherein the second color indicates whether the first or second gradients is the one gradient that exceeds a threshold.

A13. The method of any of A1-A12, wherein marking the first point comprises displaying a graphical indicator at the first point on the three-dimensional model.

A14. The method of any of A1-A13, further comprising calculating a plurality of signal intensity gradients, each signal intensity gradient corresponding to a point on the surface of the three dimensional model.

A15. The method of A14, further comprising determining whether each of the plurality of signal intensity gradients exceeds a threshold.

A16. The method of A15, further comprising determining whether a minimum number of signal intensity gradients exceeding a threshold is met.

A17. The method of A16, further comprising reprocessing the imaging data to create a new three-dimensional model if the minimum number is not met.

A18. The method of A16 or A17, further comprising displaying an alert to an operator if the minimum number is not met.

A19. The method of any of A16-A18, further comprising weighting signal intensity gradients corresponding to points of interest in the three-dimensional model before determining if the minimum number is met.

A20. The method of A19, wherein the points of interest correspond to contact points between patient-matched implants and the modeled bone.

A21. The method of A19 or A20, wherein the points of interest correspond to points located in areas on the modeled bone that exhibit variation among patients.

A22. The method of any of A1-A21, further comprising displaying a first vector line extending from the surface of the three-dimensional model at the first point.

A23. The method of A22, further comprising receiving a first user selection of the first point, and displaying the first vector line in response to the first user selection.

A24. The method of A23, further comprising receiving a second user selection of an alternate point on the surface of the three-dimensional model after the first vector line is displayed, and displaying a second vector line extending from the surface of the three-dimensional model at the alternate point in response to the second user selection.

A25. The method of any of A1-A24, wherein the first vector line is normal to the surface at the first point.

B1. A method for indicating accuracy of image segmentation in a patient model, the method comprising:
creating a three-dimensional bone surface model of a portion of a patient's bone from imaging data;
determining curvature of the modeled bone surface at a plurality of points in the three-dimensional model; and
marking each of the plurality of points in the three-dimensional with an indication whether each point is located within a concave or convex portion of the surface.

B2. The method of B1, wherein marking each of the plurality of points comprises displaying points located within a concave portion of the surface in a first color and displaying points located within a convex portion of the surface in a second color.

B3. The method of B1 or B2, further comprising identifying transition points between concave and convex portions of the surface.

B4. The method of B3, further comprising marking each of the transition points in the three-dimensional model.

B5. The method of B4, wherein marking each of the transition points comprises displaying a graphical indicator at each of the transition points.

B6. The method of B4 or B5, wherein marking each of the transition points comprises displaying each of the transition points in a color that is different than colors of concave and convex portions of the model.

B7. The method of any of B3-B6, further comprising determining if a minimum number of transition points is met.

B8. The method of B7, further comprising reprocessing the imaging data to create a new three-dimensional model if the minimum number is met.

B9. The method of B7 or B8, further comprising displaying an alert to an operator if the minimum number is met.

B10. The method of any of B7-B9, further comprising weighting points of interest in the three-dimensional model before determining if the minimum number is met.

B11. The method of B10, wherein the points of interest are located in areas of the model that are not expected to contain transition points.

C1. A system for indicating accuracy of image segmentation in a patient model, the system comprising:
means for creating a three-dimensional bone surface model of a portion of a patient's bone from imaging data;
means for calculating a first signal intensity gradient between a first point on a surface of the three-dimensional model and a second point spaced from the surface along a line extending from the surface at the first point; and
means for marking the first point on the three-dimensional model if the first gradient exceeds a first threshold.

C2. The system of C1, wherein the second point is spaced from the surface at a location outside the modeled bone.

C3. The system of C1, wherein the second point is spaced from the surface at a location within the modeled bone.

C4. The system of any of C1, further comprising means for calculating a second signal intensity gradient between the first point and a third point spaced from the surface along the line.

C5. The system of C4, wherein:
the second point is spaced from the surface at a location outside the modeled bone;
the third point is spaced from the surface at a location within the modeled bone;
the first gradient indicates a signal intensity change outward from the surface; and
the second gradient indicates a signal intensity change inward from the surface.

C6. The system of C4 or C5, further comprising means for determining whether each of the first and second gradients exceeds a threshold.

C7. The system of C6, further comprising means for determining whether each of the first and second gradients exceeds the first threshold.

C8. The system of C6, further comprising:
means for determining whether the first gradient exceeds the first threshold; and
means for determining whether the second gradient exceeds a second threshold.

C9. The system of any of C6-C8, wherein the means for marking the first point comprises means for marking the first point if both of the first and second gradients exceed a threshold.

C10. The system of any of C6-C8, wherein the means for marking the first point comprises means for marking the first point if either one of the first and second gradients exceeds a threshold.

C11. The system of any of C6-C10, wherein the means for marking the first point comprises means for displaying the first point in a first color if both of the first and second gradients exceed a threshold, means for displaying the first point in a second color if only one of the first and second gradients exceeds a threshold, and means for displaying the first point in a third color if neither of the first and second gradients exceeds a threshold.

C12. The system of C11, wherein the second color indicates whether the first or second gradients is the one gradient that exceeds a threshold.

C13. The system of any of C1-C12, wherein the means for marking the first point comprises means for displaying a graphical indicator at the first point on the three-dimensional model.

C14. The system of any of C1-C13, further comprising means for calculating a plurality of signal intensity gradients, each signal intensity gradient corresponding to a point on the surface of the three dimensional model.

C15. The system of C14, further comprising means for determining whether each of the plurality of signal intensity gradients exceeds a threshold.

C16. The system of C15, further comprising means for determining whether a minimum number of signal intensity gradients exceeding a threshold is met.

C17. The system of C16, further comprising means for reprocessing the imaging data to create a new three-dimensional model if the minimum number is not met.

C18. The system of C16 or C17, further comprising means for displaying an alert to an operator if the minimum number is not met.

C19. The system of any of C16-C18, further comprising means for weighting signal intensity gradients corresponding to points of interest in the three-dimensional model before determining if the minimum number is met.

C20. The system of C19, wherein the points of interest correspond to contact points between patient-matched implants and the modeled bone.

C21. The system of C19 or C20, wherein the points of interest correspond to points located in areas on the modeled bone that exhibit variation among patients.

C22. The system of any of C1-C21, further comprising means for displaying a first vector line extending from the surface of the three-dimensional model at the first point.

C23. The system of C22, further comprising means for receiving a first user selection of the first point, and means for displaying the first vector line in response to the first user selection.

C24. The system of C23, further comprising means for receiving a second user selection of an alternate point on the surface of the three-dimensional model after the first vector line is displayed, and means for displaying a second vector line extending from the surface of the three-dimensional model at the alternate point in response to the second user selection.

C25. The system of any of C1-C24, wherein the line is normal to the surface at the first point.

D1. A system for indicating accuracy of image segmentation in a patient model, the system comprising:
means for creating a three-dimensional bone surface model of a portion of a patient's bone from imaging data;
means for determining curvature of the modeled bone surface at a plurality of points in the three-dimensional model; and
means for marking each of the plurality of points in the three-dimensional with an indication whether each point is located within a concave or convex portion of the surface.

D2. The system of D1, wherein the means for marking each of the plurality of points comprises means for displaying points located within a concave portion of the surface in a first color and means for displaying points located within a convex portion of the surface in a second color.

D3. The system of D1 or D2, further comprising means for identifying transition points between concave and convex portions of the surface.

D4. The system of D3, further comprising means for marking each of the transition points in the three-dimensional model.

D5. The system of D4, wherein the means for marking each of the transition points comprises means for displaying a graphical indicator at each of the transition points.

D6. The system of D4 or D5, wherein the means for marking each of the transition points comprises means for displaying each of the transition points in a color that is different than colors of concave and convex portions of the model.

D7. The system of any of D3-D6, further comprising means for determining if a minimum number of transition points is met.

D8. The system of D7, further comprising means for reprocessing the imaging data to create a new three-dimensional model if the minimum number is met.

D9. The system of D7 or D8, further comprising means for displaying an alert to an operator if the minimum number is met.

D10. The system of any of D7-D9, further comprising means for weighting points of interest in the three-dimensional model before determining if the minimum number is met.

D11. The system of D10, wherein the points of interest are located in areas of the model that are not expected to contain transition points.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The application of which this description and claims form part may be used as a basis for priority in respect of any subsequent application. The claims of such subsequent application may be directed to any feature or combination of features described herein. They may take the form of product, method or use claims and may include, by way of example and without limitation, one or more of the following claims.

The invention claimed is:
1. A system for indicating accuracy of image segmentation in a patient model, the system comprising:
a processor; and
a non-transitory, processor-readable storage medium in communication with the processor, wherein the non-transitory, processor-readable storage medium com- prises one or more programming instructions that, when executed, cause the processor to:
create a three-dimensional bone surface model of a portion of a patient's bone from imaging data;
evaluate a first signal intensity gradient between a first point on a surface of the three-dimensional bone surface model and a second point spaced from the surface along a line extending from the surface at the first point; and
mark the first point on the three-dimensional bone surface model with a first indicium model if the first signal intensity gradient exceeds a first threshold.

2. The system of claim 1, wherein the second point is spaced from the surface at a location outside the modeled bone.

3. The system of claim 1, wherein the second point is spaced from the surface at a location within the modeled bone.

4. The system of claim 1, wherein the non-transitory, processor-readable storage medium further comprises one or more programming instructions that, when executed, cause the processor to: calculate a second signal intensity gradient between the first point and a third point spaced from the surface along the line.

5. The system of claim 4, wherein:
the second point is spaced from the surface at a location outside the modeled bone;
the third point is spaced from the surface at a location within the modeled bone;
the first signal intensity gradient indicates a signal intensity change outward from the surface; and
the second signal intensity gradient indicates a signal intensity change inward from the surface.

6. The system of claim 4, wherein the non-transitory, processor-readable storage medium further comprises one or more programming instructions that, when executed, cause the processor to: determine whether each of the first and second signal intensity gradients exceeds a threshold.

7. The system of claim 6, wherein the non-transitory, processor-readable storage medium further comprises one or more programming instructions that, when executed, cause the processor to: determine whether each of the first and second signal intensity gradients exceeds the first threshold.

8. The system of claim 6, wherein the non-transitory, processor-readable storage medium further comprises one or more programming instructions that, when executed, cause the processor to:
determine whether the first signal intensity gradient exceeds the first threshold; and
determine whether the second signal intensity gradient exceeds a second threshold.

9. The system of claim 1, wherein the first signal intensity gradient comprises an absolute value of the difference between the first signal intensity value of the imaging data at the first point and the second signal intensity value of the imaging data at the second point.

10. The system of claim 1, wherein the non-transitory, processor-readable storage medium further comprises one or more programming instructions that, when executed, cause the processor to: mark the first point on the three-dimensional bone surface model with a second indicium if the second signal intensity gradient does not exceed the first threshold.

11. The system of claim 10, wherein the first indicium is a first color and the second indicium is a second color.

12. The system of claim 1, wherein the non-transitory, processor-readable storage medium further comprises one or more programming instructions that, when executed, cause the processor to:
evaluate a plurality of signal intensity gradients from points on the surface of the three-dimensional model, the plurality of signal intensity gradients including the first signal intensity gradient;
determine a number of the plurality of signal intensity gradients that exceed the first threshold; and
perform a subsequent process in response to determining that the number does not exceed a minimum threshold of acceptable gradients, wherein the subsequent process comprises one or more of:
reprocessing the imaging data to create a new three-dimensional bone surface model based on a different processing technique used to generate the three-dimensional bone surface model; and
generating an alert message indicating that the minimum threshold of acceptable gradients has not been met.

13. A system for assessing the accuracy of a three-dimensional bone surface model, the system comprising:
a processor; and
a non-transitory, processor-readable storage medium in communication with the processor, wherein the non-transitory, processor-readable storage medium comprises one or more programming instructions that, when executed, cause the processor to:
create the three-dimensional bone surface model of a portion of a patient's bone from imaging data;
determine a curvature of the three-dimensional bone surface model at a plurality of points along a surface of the three-dimensional bone surface model;
identify the curvature at each of the plurality of points as convex or concave; and
mark one or more transition portions of the surface, wherein each transition portion of the surface is defined between a first point of the plurality of points and a second point of the plurality of points, wherein the first point and the second point are adjacent to each other along the surface, and wherein the first point has a concave curvature and the second point has a convex curvature.

14. The system of claim 13, wherein the non-transitory, processor-readable storage medium further comprises one or more programming instructions that, when executed, cause the processor to: obtain the imaging data, wherein the imaging data comprises one or more of magnetic resonance imaging (MRI) data and computed tomography (CT) scan data.

15. The system of claim 13, wherein the non-transitory, processor-readable storage medium further comprises one or more programming instructions that, when executed, cause the processor to: identify a transition curve that establishes a boundary between one or more points of the plurality of points having a concave curvature and one or more points of the plurality of points having a convex curvature.

16. The system of claim 13, wherein the non-transitory, processor-readable storage medium further comprises one or more programming instructions that, when executed, cause the processor to: identify an inaccuracy in the marked three-dimensional bone surface model based on the curvatures and the one or more transition portions.

17. The system of claim 16, wherein identifying an inaccuracy comprises determining whether a number of transition portions exceeds a threshold count.

\* \* \* \* \*